US008715709B2

(12) United States Patent
Huang et al.

(10) Patent No.: US 8,715,709 B2
(45) Date of Patent: May 6, 2014

(54) SUSTAINED RELEASE INTRAOCULAR IMPLANTS AND METHODS FOR TREATING OCULAR NEUROPATHIES

(75) Inventors: Glenn T. Huang, Fremont, CA (US); Thierry Nivaggioli, Los Altos Hills, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/955,630

(22) Filed: Nov. 29, 2010

(65) Prior Publication Data

US 2011/0091520 A1    Apr. 21, 2011

Related U.S. Application Data

(62) Division of application No. 10/836,880, filed on Apr. 30, 2004, now abandoned.

(51) Int. Cl.
*A61K 31/5377* (2006.01)
*A61F 2/14* (2006.01)
*A61P 27/02* (2006.01)

(52) U.S. Cl.
USPC ......... 424/426; 514/237.5; 514/651; 424/427

(58) Field of Classification Search
None
See application file for complete search history.

(56) References Cited

U.S. PATENT DOCUMENTS

| | | | |
|---|---|---|---|
| 3,845,770 A | 11/1974 | Theeuwes et al. |
| 3,916,899 A | 11/1975 | Theeuwes et al. |
| 4,008,864 A | 2/1977 | Torphammar et al. |
| 4,014,335 A | 3/1977 | Arnold |
| 4,052,505 A | 10/1977 | Higuchi et al. |
| 4,057,619 A | 11/1977 | Higuchi et al. |
| 4,063,064 A | 12/1977 | Saunders et al. |
| 4,088,864 A | 5/1978 | Theeuwes et al. |
| 4,144,317 A | 3/1979 | Higuchi et al. |
| 4,158,005 A | 6/1979 | Bodor et al. |
| 4,186,184 A | 1/1980 | Zaffaroni |
| 4,190,642 A | 2/1980 | Gale et al. |
| 4,200,098 A | 4/1980 | Ayer et al. |
| 4,281,654 A | 8/1981 | Shell et al. |
| 4,285,987 A | 8/1981 | Ayer et al. |
| 4,303,637 A | 12/1981 | Shell et al. |
| 4,304,765 A | 12/1981 | Shell et al. |
| 4,327,725 A | 5/1982 | Cortese et al. |
| 4,396,625 A | 8/1983 | Yamamori et al. |
| 4,425,346 A | 1/1984 | Horlington |
| 4,474,451 A | 10/1984 | Mizokami |
| 4,478,818 A | 10/1984 | Shell et al. |
| 4,494,274 A | 1/1985 | Thurlow |
| 4,521,210 A | 6/1985 | Wong |
| 4,599,353 A | 7/1986 | Bito |
| 4,649,151 A | 3/1987 | Dougherty et al. |
| 4,656,186 A | 4/1987 | Bommer et al. |
| 4,668,506 A | 5/1987 | Bawa |
| 4,675,338 A | 6/1987 | Bommer et al. |
| 4,693,885 A | 9/1987 | Bommer et al. |
| 4,712,500 A | 12/1987 | Montandon |
| 4,853,224 A | 8/1989 | Wong |
| 4,863,457 A | 9/1989 | Lee |
| 4,865,846 A | 9/1989 | Kaufman |
| 4,866,168 A | 9/1989 | Dougherty et al. |
| 4,932,934 A | 6/1990 | Dougherty et al. |
| 4,935,498 A | 6/1990 | Sessler et al. |
| 4,959,217 A | 9/1990 | Sanders et al. |
| 4,968,715 A | 11/1990 | Dougherty et al. |
| 4,981,871 A | 1/1991 | Abelson |
| 4,997,652 A | 3/1991 | Wong |
| 5,002,962 A | 3/1991 | Pandey et al. |
| 5,017,579 A | 5/1991 | Gubin et al. |
| 5,019,400 A | 5/1991 | Gombotz et al. |
| 5,028,621 A | 7/1991 | Dougherty et al. |
| 5,034,413 A | 7/1991 | Chan et al. |
| 5,075,115 A | 12/1991 | Brine |
| 5,089,509 A | 2/1992 | Chandraratna |
| 5,093,349 A | 3/1992 | Pandey et al. |
| 5,100,431 A | 3/1992 | Buster et al. |
| 5,164,188 A | 11/1992 | Wong |
| 5,169,638 A | 12/1992 | Dennis et al. |
| 5,171,741 A | 12/1992 | Dougherty |
| 5,173,504 A | 12/1992 | Dougherty |
| 5,190,966 A | 3/1993 | Dougherty |
| 5,198,460 A | 3/1993 | Pandey et al. |

(Continued)

FOREIGN PATENT DOCUMENTS

| | | |
|---|---|---|
| CA | 1333770 | 1/1995 |
| EP | 0364417 | 4/1990 |

(Continued)

OTHER PUBLICATIONS

Anderson et al., "An Injectable Sustained Release Fertility Control System", *Contraception* vol. 13, pp. 375-384, (1976).

Baker, R., "Controlled Release of Biologically Active Agents", A Wiley-Interscience Publication, p. 73-75 (1987).

Bito, L. Z., *Applied Pharmacology in the Medical Treatment*, Drance, S. M. and Neufeld, A. H. eds., New York, Grune & Siration, 1984, pp. 477-505.

Bito, L. Z., "Prostaglandins. Old Concepts and News Perspectives" Arch Ophthalmol. vol. 105, pp. 1036-1039 (1987).

Bodor, N. et al., "A comparison of intraocular pressure elevating activity of lotaprednoletabonate and dexamethasone in rabbits" *Current Eye Research* 11:525-30 (1992).

(Continued)

*Primary Examiner* — Kyle Purdy
(74) *Attorney, Agent, or Firm* — Jennifer Cheng; Joel B. German; Debra D. Condino

(57) ABSTRACT

Biocompatible intraocular implants include a beta adrenergic receptor antagonist and a polymer associated with the beta adrenergic receptor antagonist to facilitate release of the beta adrenergic receptor antagonist into an eye for an extended period of time. The beta adrenergic receptor antagonist may be associated with a biodegradable polymer matrix, such as a matrix of a two biodegradable polymers. The implants may be placed in an eye to treat one or more ocular conditions, such as an ocular neuropathies, for example, various forms of glaucoma.

1 Claim, 8 Drawing Sheets

(56) References Cited

U.S. PATENT DOCUMENTS

| | | | |
|---|---|---|---|
| 5,268,178 A | 12/1993 | Calhoun et al. | |
| 5,275,820 A | 1/1994 | Chang | |
| 5,300,114 A | 4/1994 | Gwon et al. | |
| 5,314,905 A | 5/1994 | Pandey et al. | |
| 5,356,629 A | 10/1994 | Sander et al. | |
| 5,378,475 A | 1/1995 | Smith et al. | 424/473 |
| 5,385,887 A | 1/1995 | Yim et al. | |
| 5,438,071 A | 8/1995 | Clauss et al. | |
| 5,443,505 A | 8/1995 | Wong et al. | |
| 5,459,159 A | 10/1995 | Pandey et al. | |
| 5,466,233 A | 11/1995 | Weiner et al. | |
| 5,501,856 A | 3/1996 | Ohtori et al. | |
| 5,504,074 A | 4/1996 | D'Amato et al. | |
| 5,587,371 A | 12/1996 | Sessler et al. | |
| 5,587,479 A | 12/1996 | Makovec et al. | |
| 5,597,897 A | 1/1997 | Ron et al. | |
| 5,655,832 A | 8/1997 | Pelka et al. | |
| 5,656,297 A | 8/1997 | Bernstein et al. | |
| 5,688,819 A | 11/1997 | Woodward et al. | |
| 5,702,716 A * | 12/1997 | Dunn et al. | 424/422 |
| 5,707,643 A | 1/1998 | Ogura | |
| 5,766,242 A | 6/1998 | Wong et al. | |
| 5,770,589 A | 6/1998 | Billson et al. | |
| 5,776,699 A | 7/1998 | Klein et al. | |
| 5,798,349 A | 8/1998 | Levy et al. | |
| 5,824,072 A | 10/1998 | Wong | |
| 5,824,074 A | 10/1998 | Koch | |
| 5,869,079 A | 2/1999 | Wong et al. | |
| 5,877,207 A | 3/1999 | Klein et al. | |
| 5,882,682 A | 3/1999 | Rork et al. | |
| 5,906,920 A | 5/1999 | Evans et al. | |
| 5,913,884 A | 6/1999 | Trauner et al. | |
| 5,919,970 A | 7/1999 | Song et al. | |
| 5,922,773 A | 7/1999 | Lipton et al. | |
| 5,958,954 A | 9/1999 | Klein et al. | |
| 6,051,576 A | 4/2000 | Ashton et al. | |
| 6,066,675 A | 5/2000 | Wen et al. | |
| 6,074,661 A | 6/2000 | Olejnik et al. | |
| 6,217,869 B1 | 4/2001 | Meyer et al. | |
| 6,217,895 B1 | 4/2001 | Guo et al. | |
| 6,225,303 B1 | 5/2001 | Miller et al. | |
| 6,258,319 B1 | 7/2001 | Hearst et al. | |
| 6,270,492 B1 | 8/2001 | Sinofsky | |
| 6,270,749 B1 | 8/2001 | Blumenkranz et al. | |
| 6,271,220 B1 | 8/2001 | Garst et al. | |
| 6,274,614 B1 | 8/2001 | Richter et al. | |
| 6,290,713 B1 | 9/2001 | Russell | |
| 6,294,361 B1 | 9/2001 | Horowitz et al. | |
| 6,306,426 B1 | 10/2001 | Olejnik et al. | |
| 6,309,669 B1 | 10/2001 | Setterstrom et al. | |
| 6,317,616 B1 | 11/2001 | Glossop | |
| 6,319,273 B1 | 11/2001 | Chen et al. | |
| 6,331,313 B1 | 12/2001 | Wong et al. | |
| 6,357,568 B1 | 3/2002 | Chen | |
| 6,369,116 B1 | 4/2002 | Wong et al. | |
| 6,403,649 B1 | 6/2002 | Woodward et al. | |
| 6,455,062 B1 | 9/2002 | Olejnik et al. | |
| 6,482,854 B1 | 11/2002 | Lipton et al. | |
| 6,497,729 B1 | 12/2002 | Moussy et al. | |
| 6,537,568 B2 | 3/2003 | Olejnik et al. | |
| 6,548,078 B2 | 4/2003 | Guo et al. | |
| 6,565,871 B2 | 5/2003 | Roser et al. | |
| 6,573,280 B2 | 6/2003 | Dreyer | |
| 6,595,945 B2 | 7/2003 | Brown | |
| 6,699,493 B2 | 3/2004 | Wong | |
| 6,713,081 B2 | 3/2004 | Robinson et al. | |
| 6,726,918 B1 | 4/2004 | Wong et al. | |
| 6,765,012 B2 | 7/2004 | Andrews et al. | |
| 8,133,890 B2 | 3/2012 | Chang et al. | |
| 8,147,865 B2 | 4/2012 | Huang et al. | |
| 2001/0023363 A1 | 9/2001 | Harth et al. | |
| 2002/0035264 A1 | 3/2002 | Kararli et al. | |
| 2002/0040015 A1 | 4/2002 | Miller et al. | |
| 2002/0094998 A1 | 7/2002 | Burke et al. | |
| 2002/0143284 A1 * | 10/2002 | Tu et al. | 604/9 |
| 2002/0197300 A1 | 12/2002 | Schultz et al. | |
| 2003/0018078 A1 | 1/2003 | Woodward et al. | |
| 2003/0069286 A1 | 4/2003 | Chen et al. | |
| 2003/0095995 A1 | 5/2003 | Wong et al. | |
| 2003/0114460 A1 | 6/2003 | Hughes et al. | |
| 2003/0165545 A1 | 9/2003 | Huth et al. | |
| 2003/0199478 A1 | 10/2003 | Andrews et al. | |
| 2003/0225152 A1 | 12/2003 | Andrews et al. | |
| 2004/0054374 A1 | 3/2004 | Weber et al. | |
| 2004/0137059 A1 * | 7/2004 | Nivaggioli et al. | 424/468 |
| 2004/0151753 A1 * | 8/2004 | Chen et al. | 424/426 |
| 2004/0208910 A1 | 10/2004 | Ashton et al. | |
| 2005/0244458 A1 | 11/2005 | Huang et al. | |
| 2005/0244464 A1 | 11/2005 | Hughes | |
| 2005/0244465 A1 | 11/2005 | Nivaggioli et al. | |
| 2005/0244469 A1 | 11/2005 | Whitcup et al. | |
| 2007/0238732 A1 | 10/2007 | Graham et al. | |
| 2008/0145407 A1 | 6/2008 | Huang et al. | |
| 2009/0181969 A1 | 7/2009 | Chen et al. | |
| 2012/0122821 A1 | 5/2012 | Huang et al. | |
| 2013/0017243 A1 | 1/2013 | Shi et al. | |
| 2013/0116254 A1 | 5/2013 | Pujara | |
| 2013/0116255 A1 | 5/2013 | Chang et al. | |

FOREIGN PATENT DOCUMENTS

| | | |
|---|---|---|
| EP | 0430539 | 6/1991 |
| EP | 0 488 401 | 11/1991 |
| WO | WO 95/13765 | 5/1995 |
| WO | WO 96/38174 | 5/1996 |
| WO | WO 00-37056 | 6/2000 |
| WO | WO 01/30323 | 5/2001 |
| WO | WO 01/58240 | 8/2001 |
| WO | WO 02/02076 | 1/2002 |
| WO | WO 02/43785 | 6/2002 |
| WO | WO 03-024420 | 3/2003 |
| WO | WO 2004-066979 | 8/2004 |
| WO | WO 2004-066983 | 8/2004 |
| WO | WO 2005/110380 | 11/2005 |

OTHER PUBLICATIONS

Brubaker, "Mechanism of Action of Bimatoprost (Lumigan™)", Surv Ophthalmol 45 (Suppl 4): S347-S351 (2001).

Busse et al., "Tyrosine kinase inhibitors: rationale, mechanisms of action, and implications for drug resistance", Semin Oncol 28(suppl 16) 47-55 (2001).

Phillips et al., "Penetration of timolol eye drops into human aqueous humour: the first hour", *British Journal of Ophthalmology*, vol. 69, pp. 217-218 (1985).

Chen et al., "Lumiga®: A Novel Drug for Glaucoma Therapy", *Optom In Pract.*, 3:95-102 (2002).

Cheng C. K., et al., "Intravitreal sustained-release dexamethasone device in the treatment of experimental uveitis", *Invest. Ophthalmol. Vis. Sci.* 36;442-53 (1995).

Chiang et al., "Pharmacokinetics and Intraocular Pressure Lowering Effect of Timolol Preparations in Rabbit Eyes," *Journal of Ocular Pharmacology and Therapeutics*, vol. 12, No. 4, pp. 471-480, (1996).

Coleman et al., "A 3-Month Randomized Controlled Trial of Bimatoprost (LUMIGAN) versus Combined Timolol and Dorzolamide (Cosopt) in Patients with Glaucoma or Ocular Hypertension", *Ophthalmology* 110(12): 2362-8 (2003).

Conquelet et al, "Successful Photodynamic Therapy Combined with Laser Photocoagulation in Three Eyes with Classic Subloveal Choroidal Neovascularization Affecting Two Patients with Multifocal Choroiditis: Case Reports", Bull Soc. Beige Ophtalmol, 283, 69-73, 2002.

Di Colo, "Controlled drug release from implantable matrices based on hydrophobic polymers", *Biomaterials*, vol. 13, No. 12, pp. 850-856 (1992).

David L. Epstein, "Primary Open-Angle Claucoma", *Chandler and Grant's Glaucoma, Lea & Febiger*, 1986, pp. 129-181.

Fabbro et al., "Protein tyrosine kinase inhibitors: new treatment modalities?", *Current Opinion in Pharmacology*, 2:374-381 (2002).

Fotsis, et al., "The endogenous oestrogen metabolite 2-methoxycestradiol inhibits angiogenesis and suppresses tumour growth", *Nature* 1994, 368, 237.

(56) References Cited

OTHER PUBLICATIONS

Gilman, A.G., et al., eds. (1990). *Goodman and Gilman's: The Pharmacological Basis of Therapeutics*, 8th Edition, Pergamon Press: New York, pp. 1447-1451.

Goel et al., "Tyrosine Kinase Inhibitors: A Clinical Persepective", *Current Oncology Reports*, 4:9-19 (2002).

Guenther, Lyn C., "Optimizing Treatment with Topical Tazarotene", *Am. J. Clin. Dermotol.*, 2003: 4(3):197-202.

Haluska et al., "Receptor tyrosine kinase inhibitors", Current Opinion in Investigational Drugs, 2(2):280-286 (2001).

Hare et al., "Efficacy and safety of memantine, an NMDA-Type Open-Channel Blocker, for reduction of retinal injury associated with experimental glaucoma in rat and monkey", Surv Ophthalmol 45(Suppl 3): S285-S289 (2001).

Hashizoe, Mototane et al. "Scieral Plug of BiodegadablePolymers for Controlled Drug Release in the Vitreous", *Arch Ophthalmol*, 1994;112 : 1380-1384.

Heller, "Biodegradable Polymers in Controlled Drug Delivery", in: *CRC Critical Reviews in Therapeutic Drug Carrier Systems*, vol. 1. (CRC Press, Boca Raton, FL, 1987), pp. 39-90.

Heller, *Hydrogels in Medicine and Pharmacy*, N. A. Peppes ed., vol. III, (CRC Press, Boca Raton, FL, 1987), pp. 137-140.

Hoyng et al., "Pharmacological Therapy for Glaucoma", Drugs, Mar. 2000, 59(3):411-34.

Hubbard et al., "Protein tyrosine kinase structure and function", Annu. Rev. Biochem., 69:373-98 (2000).

Jackanicz et al., "Polyactic Acid As A Biodegradable Carrier For Contraceptive Steroids" Contraception, vol. 8, No. 3:227-235 (1973).

Kimura, Hideya et al. "A New Vitreal Drug Delivery System using an Implantable Biodegradable Plymeric Device", *Invest Ophthalmol Vis. Sci.* 1994:35 : 2815-2819.

Kochinke et al., "Biodegradable Drug Delivery System for Uveitis Treatment", *Investigative Ophthalmology & Visual Science*, Feb. 15, vol. 37, No. 3, (1996).

Kwak, H.W. and D'Amico, D.J. "Evaluation of the retinal toxicity and pharmacokinetics of dexamethasone after intravitreal injection", *Arch. Ophthalmol.* 110:259-66 (1992).

Lai et al, "Alpha-2 adrenoceptor agonist protects retinal function after acute retinal ischemic injury in the rat", *Vis Neurosci.* 19:175-185 (2002).

Marks, R., "Topical Tazarolene: Review and Re-Evaluation", *Retinoids*, 2001; 17(3):72-74.

Maurice, D. M. "Micropharmaceutics of the eye", *Ocular Inflammation Ther.* 1:97-102 (1983).

Miller et al., "Degradation Rates of Oral Resorbable Implants (Polytactates and Polyglycolates): Rate Modification with Changes in PLA/PGA Copolymer Ratios", *J. Biomed. Materials Res.* vol. 11, pp. 711-719 (1977).

Miller et al., "Synthesis and Structure-Activity Profiles of A-Homoestranes, the Estratopones", J. Med. Chem., 40:3836-3841 (1997).

Olsen, T.W. et al. "Human scleral permeability: effects of age, cryotherapy, transscleral diode laser, and surgical thinning", *Invest. Ophthalmol. Vis. Sci.* 36:1893-1903 (1995).

Phillips et al., "Efficacy of 0.1% Tazarotene Cream for the Treatment of Photodamage", *Arch Dermatol*, Nov. 2002, 138(11): 1486-1493.

Pribluda et al., "2-Methoxyestradiol: An endogenous antiangiogenic and antiproliferative drug candidate", *Cancer and Metastasis Reviews*, 19: 173-179 (2000).

Quigley et al., "The mechanism of optic nerve damage in experimental acute intraocular pressure elevation", *Invest. Ophthalmol. Vis. Sci.* 19:505 (1980).

Rao, N.A. et al. (1997). "Intraocular inflammation and uveitis", in: *Basic and Clinical Science Course* (San Francisco: American Academy of Ophthalmology, 1997-1998), Section 9, pp. 57-80, 102-103, 152-156.

Renfro, L. et al. "Ocular effects of topical and systemic steroids", *Dermatologic Clinics* 10:505-12 (1992).

Schuettauf et al., "Effects of anti-glaucoma medications on ganglion cell survival: the DBA/2J mouse model", *Vision Res.*, 42(20):2333-7 (2002).

Schumacher et al., "The Physiological Estrogen metabolite 2-methoxyestradiol reduced tumor growth and induces apoptasis in human solid tumors", *J Cancer Res Clin Oncol.*, 127:405-410 (2001).

Schwartz, B. "The response of ocular prsesure to corticosteroids", *Ophthalmol. Clin. North Am.* 6:929-89 (1966).

Skalka, H.W. et al. "Effect of corticosteroids on cataract formation", *Arch. Ophthalmol.* 98:1773-7 (1980).

Starr, M. S., "Further Studies on the Effect of Prostaglandin on Intraocular Pressure in the Rabbit", *Exp. Eye Res.*, vol. 11. pp. 170-177 (1971).

Siebold et al., *Prodrug* 5. 3 (1989).

Tracy et al., "Factors affecting the degradation rate of poly(lactide-co-glycolide) microspheres in vivo and in vitro", *Biomaterials*, vol. 20, pp. 1057-1062 (1999).

Watson et al., "A Six-month, randomized, Double-masked Study Comparing Lalanoprost with Timolol in Open-angle Glaucoma and Ocular Hypertension", *Ophthalmology* vol. 103:126-137 (1996).

Wheeler, "Experimental studies of agents with potential neuroprotective properties", Acta Ophthalmol Scand, 77(229):27-28 (1999).

Wheeler et al, "Role of Alpha-2 Agonists in Neuroprotection", Surv Ophthalmol, vol. 48 (Suppl 1): S47-S51 (Apr. 2003).

WoldeMussie, "Neuroprotection of retinal ganglion cells in experimental models of glaucoma", Minerva Oftalmol, 42(2):71-8 (2000).

WoldeMussie et al., "Neuroprotective effects of memantine in different retinal injury models in rats", J Glaucoma 11(6):474-480 (2002).

Woodward et al., AGN 192024 (Lumigan®): A Synthetic Prostamide Analog that Lowers Primate Intraocular Pressure by Virtue of its Inherent Pharmacological Activity, ARVO 2002;(CD-ROM):POS.

Woodward et al., The Pharmacology of Bimatoprosl (Lumigan™), Surv Ophthalmol 45 (Suppl 4) S337-S345 (2001).

Zhou, T., et al. "Development of a multiple-drug delivery implant for intraocular management of proliferative vitreoretinopathy", *Journal of Controlled Release* 55: pp. 281-295.

Bito, L. Z. Biological Protection with Prostaglandins Cohen, M. M., ed., Boca Raton, Fla., CRC Press Inc., 1985, pp. 231-252.

Charles, et al., "Use of Bioerodible Polymers Impregnated with Mitomycin in Glaucoma Filtration Surgery in Rabbits," *Ophthalmology*, Apr. 1991. vol. 98, No. 4:503-508.

Jampel, et al, "Glaucoma Filtration Surgery in Monkeys Using 5-Fluorouridine in Polyanhydride Disk," *Arch Ophthalmol.*, Mar. 1990, vol. 108:430-435.

Lee et al., "Glaucoma Filtration Surgery in Rabbits Using Bioerodible Polymers and 5-Fluorouacil", *Ophthalmology*, Dec. 1987, vol. 94, No. 12, pp. 1523-1530.

Lee et al., "The Use of Bioerodible Polymers and 5-Fluorouracil in Glaucoma Filtration Surgery," *Investigative Ophthalmology & Visual Science*, Nov. 1986, vol. 29, No. 11:1692-1697.

Smith et al., "Sustained-Release Subconjunctival 5-Fluorouracil", *Ophthalmic Surgery and Laser*, Sep. 1996, vol. 27, No. 9, pp. 763-767.

Alphagano P, Product Information, Allergan, Inc., Irvine, CA 92612, 2005.

*Company News on Call*, "Oculex Announces Positive Clinical Results for Posurdex(R). The First Biodegradable Ocular Implant in Clinical Trial", Copyright © 1996-2004 PR Newswire Association LLC.

"Lumigan® a new ocular hypotensive agent for achieving target intraocular pressures," Acta Ophthalmol Scand. Scientific Abstracts 2002, 80(4) 457 (2002).

"Lumigan found effective in early phase 3", Ocul. Surg. News, Mar. 1, 2001, 19(5):1,35.

*Physician's Desk Reference*, product information on "Alphagan®", 54 Edition, (2000) pp. 493-494.

*Physician's Desk Reference for Ophthalmol Medicines*; 30 Edition, (2002) p. 285.

Surv Ophthalmol 2002, 47(3) p. 295.

(56) References Cited

OTHER PUBLICATIONS

TAZORAC® Allergan, Product Information, Irvine, CA 92612 Jan. 2004, 8 pgs.

"Tazarotene", *Drugs Future,* 2003, 28(2) 208-209 Annual Update 2003: Dermatologic Drugs.

USP 23, NF 18 (1995) pp. 1790-1798.

U.S. Appl. No. 10/246,884, filed Sep. 18, 2002.

U.S. Appl. No. 10/259,703, filed Sep. 27, 2002.

U.S. Appl. No. 10/327,018, filed Dec. 20, 2002.

U.S. Appl. No. 10/340,237, filed Jan. 9, 2003.

U.S. Appl. No. 10/836,904, filed Apr. 30, 2004.

U.S. Appl. No. 10/836,908, filed Apr. 30, 2004.

U.S. Appl. No. 10/836,911, filed Apr. 30, 2004.

U.S. Appl. No. 10/837,142, filed Apr. 2004.

U.S. Appl. No. 10/837,143, filed Apr. 30, 2004.

U.S. Appl. No. 10/837,260, filed Apr. 30, 2004.

U.S. Appl. No. 10/837,291, filed Apr. 30, 2004.

U.S. Appl. No. 10/837,348, filed Apr. 30, 2004.

U.S. Appl. No. 10/837,356, filed Apr. 30, 2004.

U.S. Appl. No. 10/837,361, filed Apr. 30, 2004.

U.S. Appl. No. 10/837,379, filed Apr. 30, 2004.

U.S. Appl. No. 60/567,339, filed Apr. 30, 2004.

U.S. Appl. No. 60/567,423, filed Apr. 30, 2004.

Enyedi, Laura et al., *An Intravitreal Device Providing Sustained Release of Cyclosporine and Dexamethasone,* Current Eye Research (1995) pp. 549-557.

Hainsworth, Dean P. et al., *Sustained Release Intravitreal Dexamethasone,* Journal of Ocular Pharmacology and Therapeutics, (1996) vol. 12, No. 1, pp. 57-63.

Merkli A. et al., "Use of Insoluble Biodegradable Polymers in Ophthalmic Systems for the Sustained Release of Drugs", European Journal of Pharmaceutics and Biopharmaceutics, Elsevier Science Publishers B.V., Amsterdam, NL, vol. 41, No. 5, Oct. 1, 1995 pp. 271-283, XP000535194, ISSN: 0939-6411.

Wang Y. et al., "Controlled release of ethacrynic acid from poly(lactide-co-glycolide) films for glaucoma treatment", Biomaterials, Elsevier Science Publishers BV., Barking, GB, vol. 25, No. 18, Aug. 2004, pp. 4279-4285, XP004497089, ISSN: 0142-9612.

Database Biosis 'Online! Biosciences Information Service, Philadelphia, PA, US; 1993, Sturesson Cecilia et al., "Preparation of biodegradable poly(lactic-co-glycolic) acid microspheres and their in vitro release of timolol maleate", XP002339576, Database accession No. PREV199395112456, International Journal of Pharmaceutics (Amsterdam), vol. 89, No. 3, 1993, pp. 235-244, ISSN: 0378-5173.

International Search Report and the Written Opinion of the International Searching Authority in International Application No. PCT/US2005/014021, mailed Aug. 23, 2005, 17 pages.

United States Board of Patent Appeals and Interferences decision on appeal in *Ex Parte Huang et al.*, Appeal 2010-006865, U.S. Appl. No. 10/836,880, mailed Sep. 28, 2010.

U.S. Appl. No. 10/836,880, filed Apr. 30, 2004.

Sturesson et al., In International Journal of Pharmaceuticals, vol. 89 (3) 235-244, 1993.

\* cited by examiner

SUSTAINED RELEASE INTRAOCULAR IMPLANTS AND METHODS FOR TREATING OCULAR NEUROPATHIES

This application is a Divisional of application Ser. No. 10/836,880 filed on Apr. 30, 2004 now abandoned, and for which priority is claimed under 35 U.S.C. §120. The entire contents of which are hereby incorporated by reference.

BACKGROUND

The present invention generally relates to devices and methods to treat an eye of a patient, and more specifically to intraocular implants that provide extended release of a therapeutic agent to an eye in which the implant is placed, and to methods of making and using such implants, for example, to treat ocular neuropathies.

Glaucoma is a progressive optic neuropathy characterized by excavation of the optic nerve head and visual field loss in the mid-periphery. Retinal ganglion cell death and consequent axon loss on the retinal nerve fiber layer result in cupping of the optic disc and visual field defects typical for glaucoma.

A major risk factor in glaucoma is thought to be elevation of the intraocular pressure (IOP) beyond the statistical norm, i.e. 21 mm Hg. The high IOP originates from an increased resistance to drainage of aqueous humor through the trabecular meshwork.

Although different forms of glaucoma are known, the most common form is adult onset open chamber angle glaucoma (OAG), which is age related and characterized by an open angle, IOPs over 21 mm Hg, a visual field defect typical for glaucoma, and a pathologically excavated optic disc.

Beta adrenergic receptor antagonists, also known as beta-blockers, are a mainstay and a first therapy choice for glaucoma.

The available beta-blockers are typically categorized as being either nonselective (also referred to as "nonspecific"), inhibiting both $\beta_1$ and $\beta_2$-adrenoceptors, or $\beta_1$ selective, which means that $\beta_1$-adrenoceptors are preferably inhibited.

Timolol maleate, (−)-1-(tert-butylamino)-3-[(4-morpholino-1,2,5-thiadiazo-3-yl)oxy]-2-propanol maleate, (1:1) salt, is a non-selective beta-adrenergic (beta$_1$, and beta$_2$) receptor blocking agent that does not have sympathomimetic or myocardial depressant activity. Timolol maleate, when applied topically, is effective in reducing elevated intraocular pressure in most forms of glaucoma, including acute angle-closure and secondary glaucomas.

Timolol maleate has been used clinically to lower intraocular pressure for treatment of chronic OAG for approximately 30 years. It does it by inhibiting aqueous humor production, and not by increasing outflow facility. However, as with many types of eye drops, it is believed that only about one percent of the daily regiment of either one drop (Timoptic XE® 0.5% q.d., Merck and Co., Inc., Whitehouse Station, N.J.) or two drops (Timoptic® 0.5% b.i.d. Merck and Co., Inc., Whitehouse Station, N.J.) actually gets absorbed inside the eyes to provide the therapeutic level. Research studies have shown that the bioavailability of timolol maleate can be improved by increasing its residence time in the precorneal area by adding a thickening agent to the drop formulation which tends to enhance the therapeutic effect of the drops.

The following patents and additional publications include disclosure which is relevant to and/or helpful in understanding the present invention: U.S. Pat. Nos. 4,521,210; 4,853,224; 4,997,652; 5,164,188; 5,443,505; 5,501,856; 5,766,242; 5,824,072; 5,869,079; 6,074,661; 6,331,313; 6,369,116; and 6,699,493. David L. Epstein, *Chandler and Grant's Glaucoma*, Lea & Febiger, (1986) pp 129-181; *Physician's Desk Reference for Ophthalmic Medicines,* 30 Edition, (2002) p 285; Chiao-His Chiang, Jing-Ing Ho, and Jiin-Long Chen, *Journal of Ocular Pharmacology and Therapeutics*, Volume 12, Number 4, 471, (1996). Calbert I. Phillips, R. Shayle Bartholomew, Anthony M. Levy, Jeffrey Grove, and Roger Vegel, *British Journal of Ophthalmology*, Volume 69, 217, (1985). The entire disclosure of each of these documents is incorporated herein by this reference.

There is still a need for more effective formulations and techniques for administering therapeutic agents, for example, beta adengergic receptor antagonists, for example, timolol maleate, to an eye in order to enhance bioavailability of the therapeutic agent to the eye.

It would be advantageous to provide eye implantable drug delivery systems, such as intraocular implants, and methods of using such systems, that are capable of releasing a therapeutic agent at a sustained or controlled rate for extended periods of time and in amounts with few or no negative side effects.

SUMMARY

The present invention provides new drug delivery systems, and methods of making and using such systems, for extended or sustained drug release into an eye, for example, to achieve one or more desired therapeutic effects. The drug delivery systems are in the form of implants or implant elements that may be placed in an eye. The present systems and methods advantageously provide for extended release times of one or more therapeutic agents. Thus, the patient in whose eye the implant has been placed receives a therapeutic amount of an agent for a long or extended time period without requiring additional administrations of the agent. For example, the patient has a substantially consistent level of therapeutically active agent available for consistent treatment of the eye over a relatively long period of time, for example, on the order of at least about one week, such as between about two and about six months after receiving an implant. Such extended release times facilitate obtaining successful treatment results.

Intraocular implants in accordance with the disclosure herein comprise a therapeutic component and a drug release sustaining component associated with the therapeutic component. In accordance with a preferred embodiment of the present invention, the therapeutic component comprises, consists essentially of, or consists of, a beta adrenergic receptor antagonist. The drug release sustaining component is associated with the therapeutic component to sustain release of an amount of the beta adrenergic receptor antagonist into an eye in which the implant is placed. The amount of the beta adrenergic receptor antagonist is released into the eye for a period of time greater than about one week after the implant is placed in the eye and is effective in preventing or reducing ocular vasculopathies, such as vascular occlusions.

In one embodiment, the intraocular implants comprise a beta adrenergic receptor antagonist and a biodegradable polymer matrix. The beta adrenergic receptor antagonist is associated with a biodegradable polymer matrix that degrades at a rate effective to sustain release of an amount of the antagonist from the implant for a time sufficient to reduce or prevent an ocular vascular occlusion. The intraocular implant is biodegradable or bioerodible and provides a sustained release of the beta adrenergic receptor antagonist in an eye for extended periods of time, such as for more than one week, for example for about three months or more and up to about six months or more. In certain implants, the beta adrenergic receptor antagonist is released for about 30-35 days or less. In other implants, the beta adrenergic receptor antagonist is released for 40 days or more.

The biodegradable polymer component of the foregoing implants may be a mixture of biodegradable polymers, wherein at least one of the biodegradable polymers is a polylactic acid polymer having a molecular weight less than 64 kiloDaltons (kD). Additionally or alternatively, the foregoing implants may comprise a first biodegradable polymer of a polylactic acid, and a different second biodegradable polymer of a polylactic acid. Furthermore, the foregoing implants may comprise a mixture of different biodegradable polymers, each biodegradable polymer having an inherent viscosity in a range of about 0.3 deciliters/gram (dl/g) to about 1.0 dl/g.

The beta adrenergic receptor antagonist of the implants disclosed herein may include a β non specific antagonist, a $β_1$, selective antagonist, a $β_2$ selective antagonist, or other antagonists that are effective in treating ocular conditions. Examples of suitable β non specific antagonist include timolol, propranolol, nadolol, pindolol and derivatives thereof. Examples of $β_1$ selective antagonists include metoprolol acebutolol, alprenolol, atenolol, esmolol, and derivatives thereof. An example of a $β_2$ selective is butoxamine. In addition, the therapeutic component of the present implants may include one or more additional and different therapeutic agents that may be effective in treating an ocular condition.

A method of making the present implants involves combining or mixing the beta adrenergic receptor antagonist with a biodegradable polymer or polymers. The mixture may then be extruded or compressed to form a single composition. The single composition may then be processed to form individual implants suitable for placement in an eye of a patient.

The implants may be placed in an ocular region to treat a variety of ocular conditions, including conditions such as ocular neuropathies that affect an anterior region or posterior region of an eye. For example, the implants may be used to treat many conditions of they eye, including, without limitation, conditions associated with glaucoma.

Kits in accordance with the present invention may comprise one or more of the present implants, and instructions for using the implants. For example, the instructions may explain how to administer the implants to a patient, and types of conditions that may be treated with the implants.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

Additional aspects and advantages of the present invention are set forth in the following description and claims, particularly when considered in conjunction with the accompanying drawings.

DRAWINGS

DESCRIPTION

Figure 1:
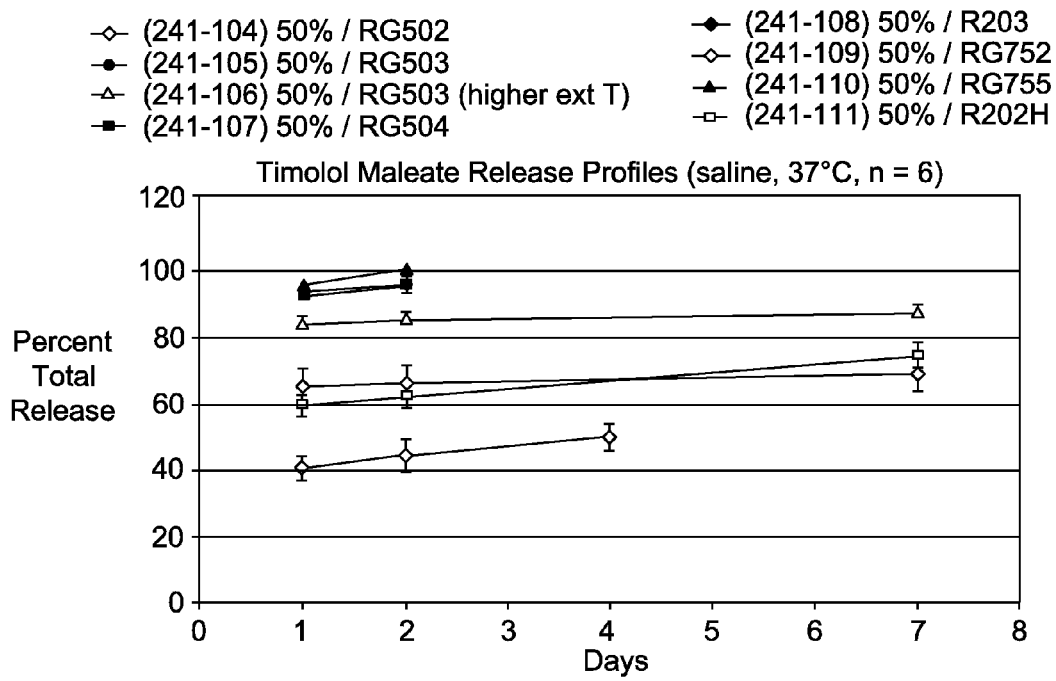
FIG. 1 is a graph of timolol maleate release profiles of drug delivery systems in accordance with the invention, comprising timolol maleate and a polymer, the systems each having 50% drug load.

As described herein, controlled and sustained administration of a therapeutic agent through the use of one or more intraocular drug delivery systems, or implants, may improve treatment of undesirable ocular conditions. The implants comprise a pharmaceutically acceptable polymeric composition and are formulated to release one or more pharmaceutically active agents, such as beta adrenergic receptor antagonists, over an extended period of time. The implants are effective to provide a therapeutically effective dosage of the agent or agents directly to a region of the eye to treat or prevent one or more undesirable ocular conditions. Thus, with a single administration, therapeutic agents will be made available at the site where they are needed and will be maintained for an extended period of time, rather than subjecting the patient to repeated injections or, in the case of self-administered drops, ineffective treatment with only limited bursts of exposure to the active agent or agents.

An intraocular implant in accordance with the disclosure herein comprises a therapeutic component and a drug release sustaining component associated with the therapeutic component. In accordance with a preferred embodiment of the present invention, the therapeutic component comprises, consists essentially of, or consists of, a beta adrenergic receptor antagonist. The drug release sustaining component is associated with the therapeutic component to sustain release of a therapeutically effective amount of the beta adrenergic receptor antagonist into an eye in which the implant is placed. The therapeutic amount of the beta adrenergic receptor antagonist is released into the eye for a period of time greater than about one week after the implant is placed in the eye.

Definitions

For the purposes of this description, we use the following terms as defined in this section, unless the context of the word indicates a different meaning.

As used herein, an "intraocular implant" refers to a device or element that is structured, sized, or otherwise configured to be placed in an eye. Intraocular implants are generally biocompatible with physiological conditions of an eye and do not cause adverse side effects. Intraocular implants may be placed in an eye without disrupting vision of the eye.

As used herein, a "therapeutic component" refers to a portion of an intraocular implant comprising one or more therapeutic agents or substances used to treat a medical condition of the eye. The therapeutic component may be a discrete region of an intraocular implant, or it may be homogenously distributed throughout the implant. The therapeutic agents of the therapeutic component are typically ophthalmically acceptable, and are provided in a form that does not cause adverse reactions when the implant is placed in an eye.

As used herein, a "drug release sustaining component" refers to a portion of the intraocular implant that is effective to provide a sustained release of the therapeutic agents of the implant. A drug release sustaining component may be a biodegradable polymer matrix, or it may be a coating covering a core region of the implant that comprises a therapeutic component.

As used herein, "associated with" means mixed with, dispersed within, coupled to, covering, or surrounding.

As used herein, an "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

As used herein, an "ocular condition" is a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

The present invention is especially useful in the treatment of the glaucoma, including any of the several different types of glaucoma, including angle-closure glaucoma, neovascular glaucoma, open-angle glaucoma and hydrophthalmos.

The terms "biodegradable" and "bioerodible" are generally used interchangeably herein.

The term "biodegradable polymer" refers to a polymer or polymers which degrade in vivo, and wherein erosion of the polymer or polymers over time occurs concurrent with or subsequent to release of the therapeutic agent. Specifically, hydrogels such as methylcellulose which act to release drug through polymer swelling are specifically excluded from the term "biodegradable polymer". The terms "biodegradable" and "bioerodible" are equivalent and are used interchangeably herein. A biodegradable polymer may be a homopolymer, a copolymer, or a polymer comprising more than two different polymeric units.

The term "treat", "treating", or "treatment" as used herein, refers to reduction or resolution or prevention of an ocular condition, ocular injury or damage, or to promote healing of injured or damaged ocular tissue.

The term "therapeutically effective amount" as used herein, refers to the level or amount of agent needed to treat an ocular condition, or reduce or prevent ocular injury or damage without causing significant negative or adverse side effects to the eye or a region of the eye.

Intraocular implants have been developed which can release drug loads over various time periods. These implants, which when inserted into an eye, such as the vitreous of an eye, provide therapeutic levels of a beta adrenergic receptor antagonist for extended periods of time (e.g., for about 1 week or more). The implants disclosed are effective in treating ocular conditions, for example ocular neuropathies such as glaucoma.

In one embodiment of the present invention, an intraocular implant comprises a biodegradable polymer matrix. The biodegradable polymer matrix is one type of a drug release sustaining component. The biodegradable polymer matrix is effective in forming a biodegradable intraocular implant. The biodegradable intraocular implant comprises a beta adrenergic receptor antagonist associated with the biodegradable polymer matrix. Preferably, the matrix degrades at a rate effective to sustain release of an amount of the beta adrenergic receptor antagonist for a time greater than about one week from the time in which the implant is placed in ocular region or ocular site, such as the vitreous of an eye.

The beta adrenergic receptor antagonist of the implant may be beta nonspecific or beta specific. In a preferred embodiment of the invention, the beta adrenergic receptor antagonist is selected from the group consisting of timolol, bexatol, levobunolol, carteolol, metiprenolol, derivatives thereof and mixtures thereof. For example, the beta adrenergic receptor antagonist comprises timolol maleate. Generally, the beta adrenergic receptor antagonist of the implants disclosed herein may include a β non specific antagonist, a $β_1$ selective antagonist, a $β_2$ selective antagonist, or other antagonists that are effective in treating ocular conditions. Examples of β non-specific antagonist include timolol, propranolol, nadolol, pindolol and derivatives thereof. Examples of $β_1$ selective antagonists include metoprolol acebutolol, alprenolol, atenolol, esmolol, and derivatives thereof. An example of a $β_2$ selective is butoxamine.

Pharmaceutically acceptable acid addition salts of the compounds of the invention are those formed from acids which form non-toxic addition salts containing pharmaceutically acceptable anions, such as the hydrochloride, hydrobromide, hydroiodide, sulfate, or bisulfate, phosphate or acid phosphate, acetate, maleate, fumarate, oxalate, lactate, tartrate, citrate, gluconate, saccharate and p-toluene sulphonate salts.

Thus, the implant may comprise a therapeutic component which comprises, consists essentially of, or consists of a timolol salt, such as timolol maleate.

The beta adrenergic receptor antagonist may be in a particulate or powder form and entrapped by the biodegradable polymer matrix. Beta adrenergic receptor antagonist particles commonly have an effective average size less than about 3000 nanometers. In certain implants, the particles may have an effective average particle size about an order of magnitude smaller than 3000 nanometers. For example, the particles may have an effective average particle size of less than about 500 nanometers. In additional implants, the particles may have an effective average particle size of less than about 400 nanometers, and in still further embodiments, a size less than about 200 nanometers.

The beta adrenergic receptor antagonist of the implant is preferably from about 10% to 90% by weight of the implant. More preferably, the beta adrenergic receptor antagonist is from about 20% to about 80% by weight of the implant. In a preferred embodiment, the beta adrenergic receptor antagonist comprises about 20% by weight of the implant, or about 26% by weight of the implant. In another embodiment, the beta adrenergic receptor antagonist comprises up to about 50% by weight of the implant.

Suitable polymeric materials or compositions for use in the implant include those materials which are compatible, that is biocompatible, with the eye so as to cause no substantial interference with the functioning or physiology of the eye. Such materials preferably are at least partially and more preferably substantially completely biodegradable or bioerodible.

Examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present implants.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyvinyl alcohol, polyesters, polyethers and combinations thereof which are biocompatible and may be biodegradable and/or bioerodible.

Some preferred characteristics of the polymers or polymeric materials for use in the present invention may include biocompatibility, compatibility with the therapeutic component, ease of use of the polymer in making the drug delivery systems of the present invention, a half-life in the physiological environment of at least about 6 hours, preferably greater than about one day, not significantly increasing the viscosity of the vitreous, and water insolubility.

The biodegradable polymeric materials which are included to form the matrix are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Equally important to controlling the biodegradation of the polymer and hence the extended release profile of the implant is the relative average molecular weight of the polymeric composition employed in the implant. Different molecular weights of the same or different polymeric compositions may be included in the implant to modulate the release profile. In certain implants, the relative average molecular weight of the polymer will range from about 9 to about 64 kD, usually from about 10 to about 54 kD, and more usually from about 12 to about 45 kD.

In some implants, copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the implant, where a more flexible implant is desirable for larger geometries. The % of polylactic acid in the polylactic acid polyglycolic acid (PLGA) copolymer can be 0-100%, preferably about 15-85%, more preferably about 35-65%. In some implants, a 50/50 PLGA copolymer is used.

The biodegradable polymer matrix of the intraocular implant may comprise a mixture of two or more biodegradable polymers. For example, the implant may comprise a mixture of a first biodegradable polymer and a different second biodegradable polymer. One or more of the biodegradable polymers may have terminal acid groups.

Release of a drug from an erodible polymer is the consequence of several mechanisms or combinations of mechanisms. Some of these mechanisms include desorption for the surface of the implant, dissolution, diffusion through porous channels of the hydrated polymer and erosion. Erosion can be bulk erosion, or surface erosion, or a combination of both. As discussed herein, the matrix of the intraocular implant may release drug at a rate effective to sustain release of an amount of the beta adrenergic receptor antagonist for more than one week after implantation into an eye. In certain implants, therapeutic amounts of the beta adrenergic receptor antagonist are released for more about 30-35 days after implantation. For example, an implant may comprise timolol maleate, and the matrix of the implant releases drug at a rate effective to sustain release of a therapeutically effective amount of timolol maleate for about one month after being placed in an eye. As another example, the implant may comprise timolol maleate, and the matrix degrades at a rate effective to sustain release of a therapeutically effective amount of timolol for more than forty days, such as for about six months.

One example of the biodegradable intraocular implant comprises a beta adrenergic receptor antagonist associated with a biodegradable polymer matrix, which comprises a mixture of different biodegradable polymers. At least one of the biodegradable polymers is a polylactide having a molecular weight of about 63.3 kD. A second biodegradable polymer is a polylactide having a molecular weight of about 14 kD. Such a mixture is effective in sustaining release of a therapeutically effective amount of the beta adrenergic receptor antagonist for a time period greater than about one month from the time the implant is placed in an eye.

Another example of a biodegradable intraocular implant comprises a beta adrenergic receptor antagonist associated with a biodegradable polymer matrix, which comprises a mixture of different biodegradable polymers, each biodegradable polymer having an inherent viscosity from about 0.16 dl/g to about 1.0 dl/g. For example, one of the biodegradable polymers may have an inherent viscosity of about 0.3 dl/g. A second biodegradable polymer may have an inherent viscosity of about 1.0 dl/g. The inherent viscosities identified above may be determined in 0.1% chloroform at 25° C.

One particular implant comprises timolol maleate associated with a combination of two different polylactide polymers. The timolol maleate is present in about 20% by weight of the implant. One polylactide polymer has a molecular weight of about 14 kD and an inherent viscosity of about 0.3 dl/g, and the other polylactide polymer has a molecular weight of about 63.3 kD and an inherent viscosity of about 1.0 dl/g. The two polylactide polymers are present in the implant in a 1:1 ratio. Such an implant provides for release of the timolol for more than two months in vitro, as described herein. The implant is provided in the form of a rod or a filament produced by an extrusion process.

The release of the beta adrenergic receptor antagonist from the intraocular implant comprising a biodegradable polymer matrix may include an initial burst of release followed by a gradual increase in the amount of the beta adrenergic receptor antagonist released, or the release may include an initial delay in release of the beta adrenergic receptor antagonist followed by an increase in release. When the implant is substantially completely degraded, the percent of the beta adrenergic receptor antagonist that has been released is about one hundred. Compared to existing implants, the implants disclosed herein do not completely release, or release about 100% of the beta adrenergic receptor antagonist, until after about one week of being placed in an eye.

It may be desirable to provide a relatively constant rate of release of the beta adrenergic receptor antagonist from the implant over the life of the implant. For example, it may be desirable for the beta adrenergic receptor antagonist to be released in amounts from about 0.01 µg to about 2 µg per day for the life of the implant. However, the release rate may change to either increase or decrease depending on the formulation of the biodegradable polymer matrix. In addition, the release profile of the beta adrenergic receptor antagonist may include one or more linear portions and/or one or more non-linear portions. Preferably, the release rate is greater than zero once the implant has begun to degrade or erode.

The implants may be monolithic, i.e. having the active agent or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the drug falls within a narrow window. In addition, the therapeutic component, including the beta adrenergic receptor antagonist, may be distributed in a non-homogenous pattern in the matrix. For example, the implant may include a portion that has a greater concentration of the beta adrenergic receptor antagonist relative to a second portion of the implant.

The intraocular implants disclosed herein may have a size of between about 5 µm and about 2 mm, or between about 10 µm and about 1 mm for administration with a needle, greater than 1 mm, or greater than 2 mm, such as 3 mm or up to 10 mm, for administration by surgical implantation. The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter, or for example, the implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 μg, more preferably about 500-1000 μg. For example, an implant may be about 500 μg, or about 1000 μg. For non-human individuals, the dimensions and total weight of the implant(s) may be larger or smaller, depending on the type of individual. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Thus, implants can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The implants may be of any geometry including fibers, sheets, films, microspheres, spheres, circular discs, plaques and the like. The upper limit for the implant size will be determined by factors such as toleration for the implant, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of 0.5 μm to 4 mm in diameter, with comparable volumes for other shaped particles.

The size and form of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

The proportions of beta adrenergic receptor antagonist, polymer, and any other modifiers may be empirically determined by formulating several implants with varying proportions. A USP approved method for dissolution or release test can be used to measure the rate of release (USP 23; NF 18 (1995) pp. 1790-1798). For example, using the infinite sink method, a weighed sample of the implant is added to a measured volume of a solution containing 0.9% NaCl in water, where the solution volume will be such that the drug concentration is after release is less than 5% of saturation. The mixture is maintained at 37° C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

In addition to the beta adrenergic receptor antagonist or beta adrenergic receptor antagonists included in the intraocular implants disclosed herein, the intraocular implants may also include one or more additional ophthalmically acceptable therapeutic agents. For example, the implant may include one or more antihistamines, one or more antibiotics, one or more alpha adrenergic receptor agonists, one or more steroids, one or more antineoplastic agents, one or more immunosuppressive agents, one or more antiviral agents, one or more antioxidant agents, and mixtures thereof.

Pharmacologic or therapeutic agents which may find use in the present systems, include, without limitation, those disclosed in U.S. Pat. Nos. 4,474,451, columns 4-6 and 4,327,725, columns 7-8.

Examples of antihistamines include, and are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, chiorcyclizine, thonzylamine, and derivatives thereof.

Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, and derivatives thereof.

Examples of alpha adrenergic receptor agonists include quinoxalines, (2-imidozolin-2-ylamino) quinoxalines, 5-bromo-6-(2-imidozolin-2-ylamino) quinoxalines, derivatives thereof and mixtures thereof.

Examples of steroids include corticosteroids, such as cortisone, prednisolone, fluorometholone, dexamethasone, medrysone, loteprednol, fluazacort, hydrocortisone, prednisone, betamethasone, prednisone, methylprednisolone, riamcinolone hexacatonide, paramethasone acetate, diflorasone, fluocinonide, fluocinolone, triamcinolone, derivatives thereof, and mixtures thereof.

Examples of antineoplastic agents include adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppresive agents include cyclosporine, azathioprine, tacrolimus, and derivatives thereof.

Examples of antiviral agents include interferon gamma, zidovudine, amantadine hydrochloride, ribavirin, acyclovir, valciclovir, dideoxycytidine, phooosphonoformic acid, ganciclovir and derivatives thereof.

Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamyl-cysteine, quercitin, lactoferrin, dihydrolipoic acid, citrate,

*Ginkgo Biloba* extract, tea catechins, bilberry extract, vitamins E or esters of vitamin E, retinyl palmitate, and derivatives thereof.

Other therapeutic agents include squalamine, carbonic anhydrase inhibitors, prostamides, prostaglandins, antiparasitics, antifungals, and derivatives thereof.

The amount of active agent or agents employed in the implant, individually or in combination, will vary widely depending on the effective dosage required and the desired rate of release from the implant. Usually the agent will be at least about 1, more usually at least about 10 weight percent of the implant, and usually not more than about 80, more usually not more than about 40 weight percent of the implant.

In addition to the therapeutic component, the intraocular implants disclosed herein may include effective amounts of buffering agents, preservatives and the like. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents advantageously present in amounts sufficient to maintain a pH of the system of between about 2 to about 9 and more preferably about 4 to about 8. As such the buffering agent may be as much as about 5% by weight of the total implant. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from 0.001 to about 5% by weight and preferably 0.01 to about 2% by weight. In at least one of the present implants, a purite preservative is provided in the implant, such as when the beta adrenergic receptor antagonist is timolol. Thus, these implants may contain a therapeutically effective amount of Alphagan-P®.

In some situations mixtures of implants may be utilized employing the same or different pharmacological agents. In this way, a cocktail of release profiles, giving a biphasic or triphasic release with a single administration is achieved, where the pattern of release may be greatly varied.

Additionally, release modulators such as those described in U.S. Pat. No. 5,869,079 may be included in the implants. The amount of release modulator employed will be dependent on the desired release profile, the activity of the modulator, and on the release profile of the beta adrenergic receptor antagonist in the absence of modulator. Electrolytes such as sodium chloride and potassium chloride may also be included in the implant. Where the buffering agent or enhancer is hydrophilic, it may also act as a release accelerator. Hydrophilic additives act to increase the release rates through faster dissolution of the material surrounding the drug particles, which increases the surface area of the drug exposed, thereby increasing the rate of drug bioerosion. Similarly, a hydrophobic buffering agent or enhancer dissolve more slowly, slowing the exposure of drug particles, and thereby slowing the rate of drug bioerosion.

In certain implants, an implant comprising timolol or timolol maleate and a biodegradable polymer matrix is able to release or deliver an amount of timolol between about 0.1 mg to about 0.5 mg for about 3-6 months after implantation into the eye. The implant may be configured as a rod or a wafer. A rod-shaped implant may be derived from filaments extruded from a 720 μm nozzle and cut into 1 mg size. A wafer-shaped implant may be a circular disc having a diameter of about 2.5 mm, a thickness of about 0.127 mm, and a weight of about 1 mg.

The proposed 3-month release formulations may be sterile, and bioerodible in the form of a rod, a wafer or a microsphere containing timolol maleate within a PLA matrix or POE matrix. The implants are designed to delay the clearance of the drug and reduce the need for repeated implantation over 3-month period, thereby lowering the risk of complications.

Various techniques may be employed to produce the implants described herein. Useful techniques include, but are not necessarily limited to, solvent evaporation methods, phase separation methods, interfacial methods, molding methods, injection molding methods, extrusion methods, co-extrusion methods, carver press method, die cutting methods, heat compression, combinations thereof and the like.

Specific techniques and methods are discussed in Wong, U.S. Pat. No. 4,997,652. Extrusion methods may be used to avoid the need for solvents in manufacturing. When using extrusion methods, the polymer and drug are chosen so as to be stable at the temperatures required for manufacturing, usually at least about 85 degrees Celsius. Extrusion methods use temperatures of about 25 degrees C. to about 150 degrees C., more preferably about 65 degrees C. to about 130 degrees C. An implant may be produced by bringing the temperature to about 60 degrees C. to about 150 degrees C. for drug/polymer mixing, such as about 130 degrees C., for a time period of about 0 to 1 hour, 0 to 30 minutes, or 5-15 minutes. For example, a time period may be about 10 minutes, preferably about 0 to 5 min. The implants are then extruded at a temperature of about 60 degrees C. to about 130 degrees C., such as about 75 degrees C.

In addition, the implant may be coextruded so that a coating is formed over a core region during the manufacture of the implant.

Compression methods may be used to make the implants, and typically yield implants with faster release rates than extrusion methods. Compression methods may use pressures of about 50-150 psi, more preferably about 70-80 psi, even more preferably about 76 psi, and use temperatures of about 0 degrees C. to about 115 degrees C., more preferably about 25 degrees C.

The implants of the present invention may be inserted into the eye, for example the vitreous chamber of the eye, by a variety of methods, including placement by forceps or by trocar following making a 2-3 mm incision in the sclera. One example of a device that may be used to insert the implants into an eye is disclosed in U.S. patent application Ser. No. 10/246,884, filed on Sep. 18, 2002, which is U.S. Patent Publication No. 2004/0054374, the disclosure of which is incorporated herein in its entirety by this reference. The method of placement may influence the therapeutic component or drug release kinetics. For example, delivering the implant with a trocar may result in placement of the implant deeper within the vitreous than placement by forceps, which may result in the implant being closer to the edge of the vitreous. The location of the implant may influence the concentration gradients of therapeutic component or drug surrounding the element, and thus influence the release rates (e.g., an element placed closer to the edge of the vitreous may result in a slower release rate).

The present implants are configured to release an amount of beta adrenergic receptor antagonist in an eye for a period of time to minimize an ocular neuropathy, such as open angle glaucoma. By implanting the beta adrenergic receptor antagonist-containing implants into the vitreous of an eye, it is believed that the antagonist is effective to reduce IOP of the eye.

EXAMPLE 1

Manufacture of Implants Containing Timolol and a Biodegradable Polymer Matrix Biodegradable drug delivery systems, or implants, in accordance with the invention, were made by combining timolol maleate or timolol freebase with a biodegradable polymer composition.

More specifically, implants were made in forms of pellets and wafers. For example, drug delivery system pellet elements, typically cylindrical in form, were made as pellets having sizes and weights of 1.8 mm L x about 0.72 mm diameter and 900 μg to 11 00 μg by weight, or pellets having sizes and weights of 1.2 mm L x 0.38 mm diameter and 216 to 264 μg by weight. Drug delivery system wafer elements were made as generally circular wafers having a size and weight of 0.13 mm thickness×2.5 mm diameter and 900 μg to 1100 μg weight.

Different formulations of such pellet elements and wafer elements were made and tested as described hereinafter. In each formulation, an active pharmaceutical ingredient (API), timolol maleate, was combined with a polymer.

The polymers chosen for the formulation work were obtained from Boehringer Ingelheim. The polymers were: Resomer RG502, RG502H, RG503, RG504, RG505, RG506, RG752, RG755, RG756, RG858, R202H, R203, and R206. Resomer RG502, RG502H, RG503, RG504, RG505, and RG506 are all 50:50 poly (D, L-lactide-co-glycolide) with inherent viscosities of 0.2, 0.2, 0.4, 0.5, 0.7 and 0.8 dL/g, respectively. RG752, RG755, and RG756 are 75:25 poly (D,L lactide-co-glycolide) with inherent viscosities of 0.2, 0.6, and 0.8 dL/g, respectively. RG858 is 85:15 poly (D,L-lactide-co-glycolide) with inherent viscosity of 1.4 dL/g, and R203 and R206 are poly (D,L-lactide) with inherent viscosities of 0.3 and 1.0 dL/g, respectively. Finally, R202H is poly (D,L-lactide) with inherent viscosity of 0.2 and acid end.

For each formulation, the drug and polymer were combined in a stainless steel mortar and mixed by means of a Turbula shaker set at 96 RPM for 15 minutes. The powder blend was scraped off the wall of the mortar and then remixed for an additional 15 minutes. The mixed powder blend was transferred into a Teflon beaker and heated to a molten state at 95° C. for a total of about 30 to 60 minutes, in ten 3-6 minute intervals, to form a homogeneous polymer/drug melt.

The polymer/drug melt was then made into pellets and wafers. More specifically, the melt was pelletized using a 9 gauge polytetrafluoroethylene (PTFE) tubing. The pellets were loaded into the barrel of a piston extruder and extruded at the specified core extrusion temperature into filaments, then cut into about 1 mg size pellets. The melt was made into wafers by means of a Carver press utilized at a appropriate temperature and pressure, and thereafter pressed polymer/drug sheets were cut into wafers, each weighing about 1 mg.

Testing of Implants Containing Timolol and a Biodegradable Polymer Matrix

The in-vitro drug rate release testing was performed as follows.

Each implant, either pellet or wafer, was placed into a 40 mL screw cap vial each filled with 10 mL of 0.9% saline and the vials were placed into shaken water bath at 37° C./50 rpm. At specified time points, 8 mL aliquots were removed and replaced with equal volume of fresh medium. The drug assays were performed by HPLC, which generally consists of a Waters HPLC system, including a 2690 Separation Module (or 2696 Separation Module), and a 2996 Photodiode Array Detector. A Metachem Inertsil, RPC-18, 5 μm; 4.6×250 mm column was used for separation, and detector was set at 295 nm. The mobile phase was (25:75) acetonitrile-0.01 M $KH_2PO_4$, pH=2.8, with flow rate of 1 mL/min and a total run time of 6 min per sample. The release rates were determined by calculating the amount of drug being released in a given volume of medium over time in μg/day.

The drug assays for the in-vivo samples was performed under the same HPLC condition as those of in-vitro samples except the mobile phase was (20:80) acetonitrile-0.01 M $KH_2PO_4$, pH=2.8.

Implants containing a 50% drug load and various polymers were screened. Formulation screening work started out with RG502, RG503, RG504, R203, RG752, RG755, and R202H with weight average molecular weight (Mw) of 8,400; 28,300; na; 14,000; 11,200; 40,000; and 6500 daltons, respectively. Turning to FIG. 1, a graph showing timolol maleate release rate profiles for the 50% drug load implants made with these various different polymers, is shown.

Data revealed that all 50% drug load formulations exhibited very fast one day release, with half of the formulations reached release greater than about 90% at day one, while the other half of the formulations released between 40% to 85% of the timolol maleate at day one, as shown in FIG. 1.

This initial high drug release rate resulted in part because of the high solubility of timolol maleate in aqueous medium. Although not wishing to be bound by any particular theory of operation, it is believed that once the implant is in contact with the dissolution medium, the timolol maleate on the surface of the implant dissolves quickly and diffuses out of the matrix thereby leaving channels allowing more dissolution medium to diffuse inside the implant and dissolve more timolol maleate.

Timolol freebase, a non-salt form of timolol maleate, is less soluble in the same dissolution medium. With that in mind, three different formulations of timolol maleate implants were made with an equivalent of sodium carbonate added in RG502, and separately in R203 in an attempt to generate the freebase in-situ and therefore slow down the release rate of timolol. It was observed that, the release rates of these implants behaved as if no timolol freebase was being generated in-situ, as shown in Table 1.

TABLE 1

Formulations with one equivalent of $Na_2CO_3$ added (saline, 37° C., n = 6)

| Formulation # | RT # | Lot # | Timolol | Polymer | Nozzle | Size | Day 1 |
|---|---|---|---|---|---|---|---|
| 9 | 265-68 | 241-142 | 45% | RG502 | 380 um | 240 ug | 78.70% |
| 10 | 265-78 | 241-143 | 24% | RG502 | 380 um | 240 ug | 61.30% |
| 11 | 265-69 | 241-144 | 45% | R203 | 380 um | 240 ug | 94.10% |

As shown, formulations 9, 10, and 11 showed a release of approximately 79%, 61%, and 94%, respectively. After day one, this particular release study was stopped.

Figure 2:
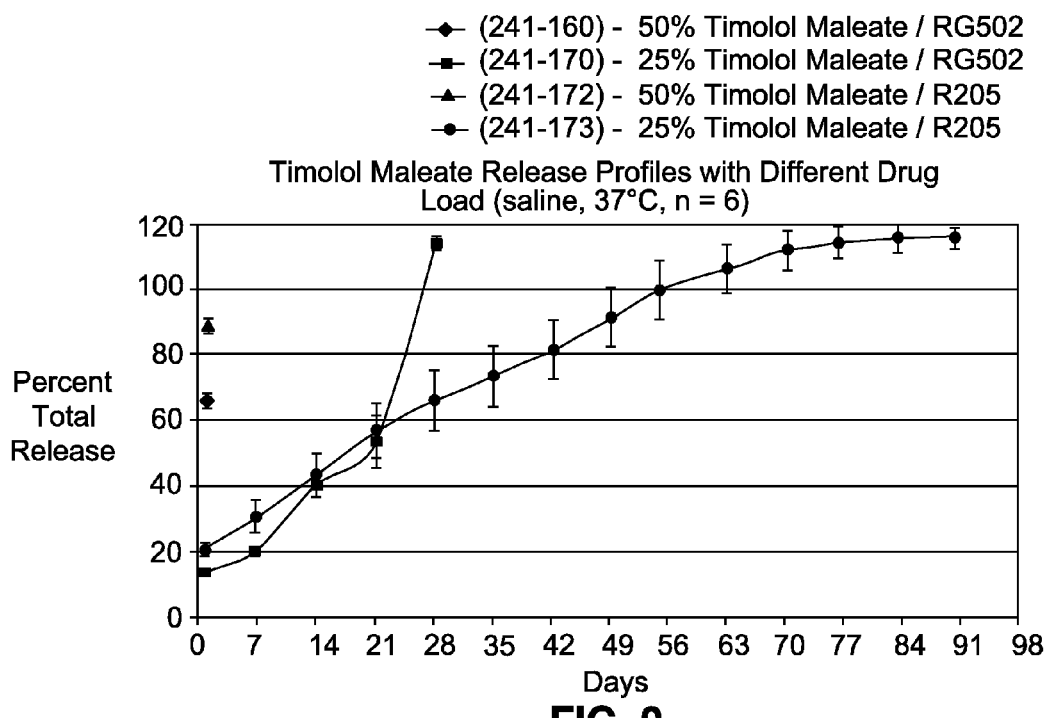
FIG. 2 is a graph of timolol maleate release profiles of drug delivery systems in accordance with the invention, comprising timolol maleate and a polymer, the systems each having 50% drug load.

Tests were performed in attempt to determine any correlation between drug load and drug release profile. Implants having drug loads of 25% and 50% timolol maleate in RG502 and in R206 were prepared. A graph of the drug release profiles is shown in FIG. 2.

It was found that by reducing the drug load by half, the release on day one was reduced by more than two folds. Day one release for 25% timolol maleate in RG502 was about 13.7%, comparing to approximately 66% for the 50% drug load samples, and day one release for 25% timolol maleate in R206 was about 20.0% comparing to about 88.4% for the 50% drug load samples.

It was observed that as the release rates dropped with lower drug load, the duration of release lengthened from one day release (50% timolol maleate in either RG502 or R206) to 28 days for 25% timolol maleate in RG502 and up to 60 days for 25% timolol maleate in R206.

Implants were made having a 10% drug load to determine if a desired six-month release could be achieved by reducing the drug load. The resulting data revealed that for 10% timolol maleate in RG502, the total release was about 10.7% on day 7 but thereafter all implants disintegrated such that only an amorphous cloud remained in the sample vials. The release study was therefore discontinued. However, the drug release of the formulation containing 10% timolol maleate in R206 was relatively slower. This release study was stopped after 98 days with a total release of about 29.1 percent, as shown in FIG. 3.

Figure 3:
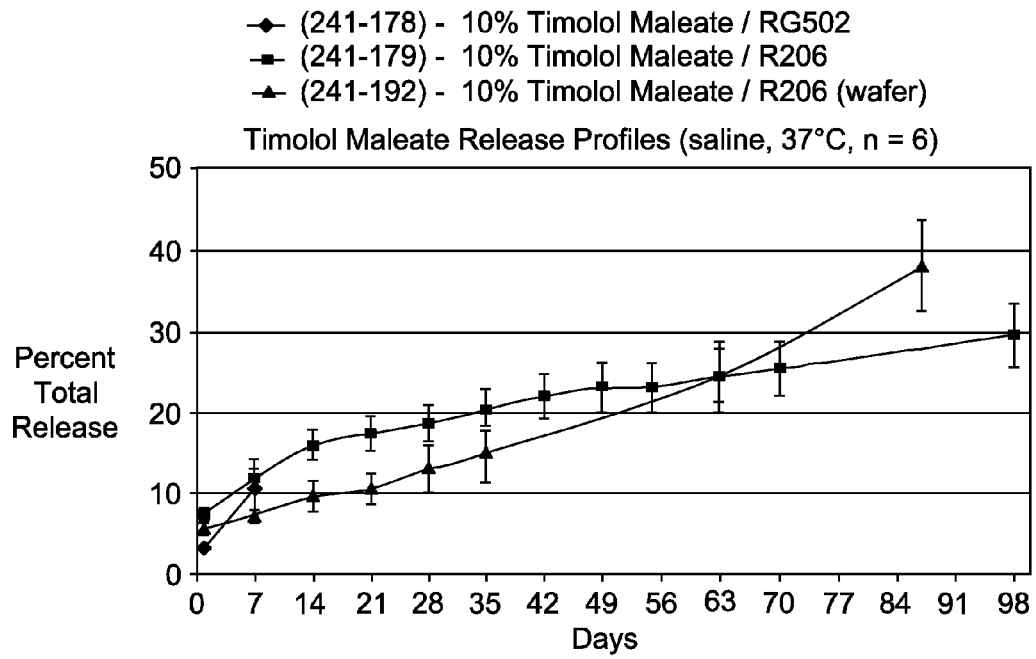
FIG. 3 is a graph of timolol maleate release profiles of drug delivery systems in accordance with the invention, comprising timolol maleate and a polymer, the systems each having 10% drug load.

It is noted that FIG. 3 also reflects release profiles of 10% timolol maleate formulation (lot 241-192) in wafer form to compare the drug release of wafers with the drug release of rods made from the same formulation. The data showed that the drug release from the wafer was initially slower than the rod, but then after day 63, a cross over occurred after which the drug release from the wafer was faster than the drug release from the rod.

During the formulation of the 10% timolol maleate in RG502 (lot 241-178) and 10% timolol maleate in R206 (lot 241-792), a 720 µm nozzle was used to extrude the filaments instead of the 380 µm that was used for all earlier formulations. Furthermore, the implant size for the 10% timolol maleate formulation was 1 mg, compared to 240 µg in the earlier formulations.

Figure 4:
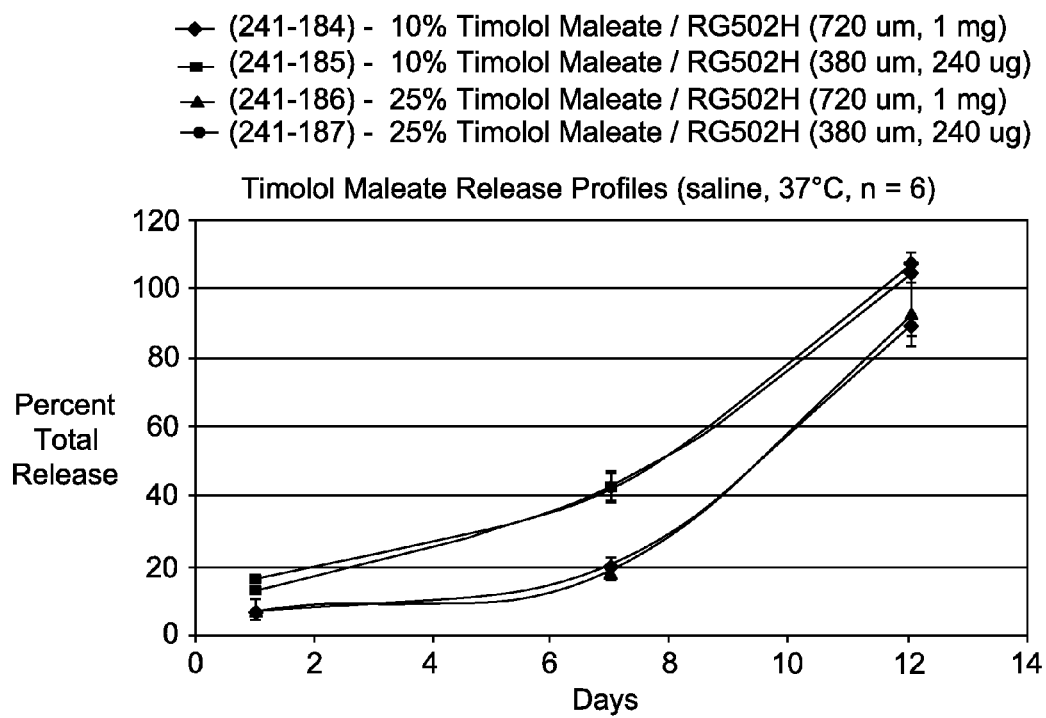
FIG. 4 is a graph of timolol maleate release profiles of drug delivery systems in accordance with the invention, the graph comparing two different sized filaments of timolol maleate and a polymer.

Another test was conducted to determine how a change in implant size would affect the rate of drug release. Four formulations were prepared using a single polymer RG502H and two different nozzles sizes of 380 µm and 720 µm. The implants were cut to a weight of 1 mg±10% for the filaments extruded from the 720 µm nozzle, and 0.24 mg±10% for the filaments extruded from the 380 µm nozzle. The release profiles of these implants of different sizes are shown in FIG. 4.

Figure 5A:
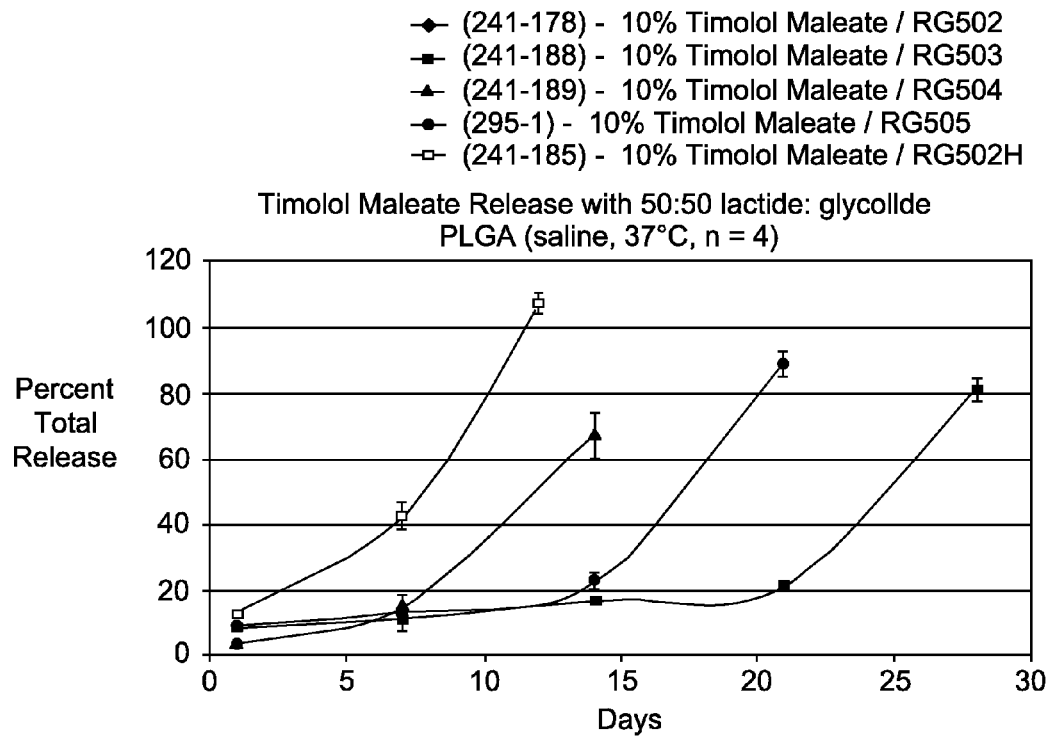
FIGS. 5A, 5B and 5C are graphs of timolol maleate release profiles of drug delivery systems in accordance with the invention, the graphs comparing release profiles of such systems comprising various drug loads and various polymer matrices.
Figure 5B:
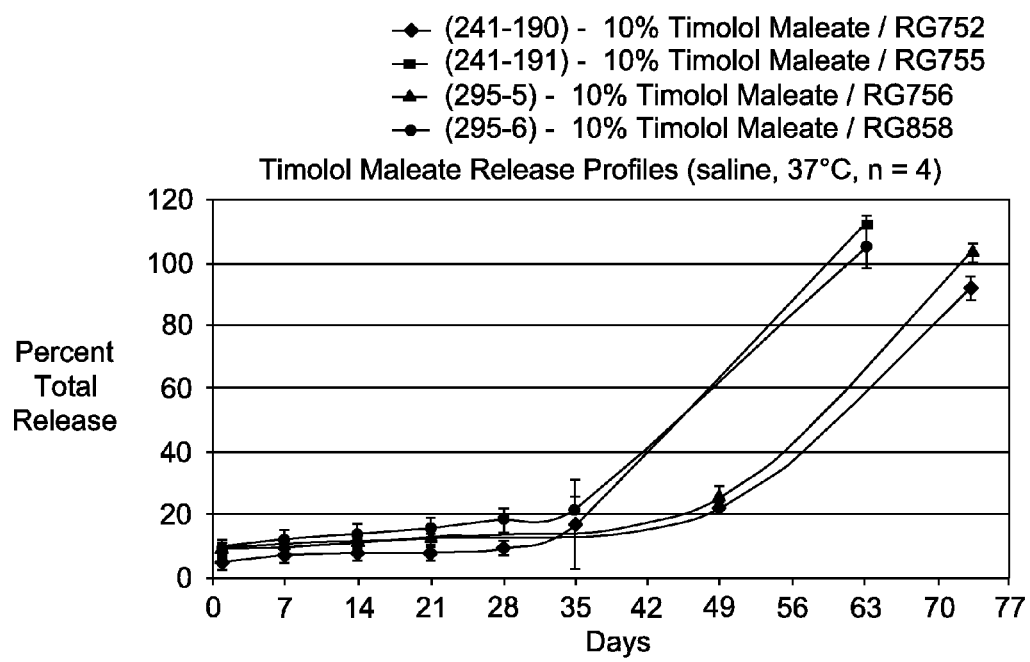
Figure 5C:
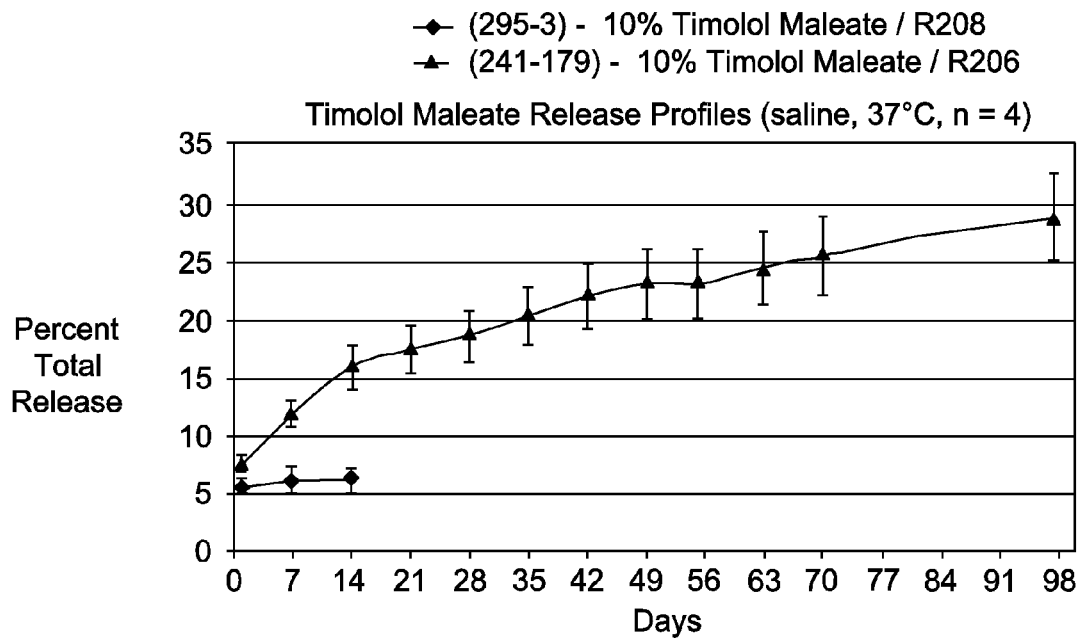

It was observed that the implants cut from a smaller diameter filament exhibited a faster drug release than the drug release from a larger diameter filament (241-185 vs. 241-184, and 241-187 vs. 241-186). However, no substantial difference was observed between implants of 10% and 25% drug load. Without wishing to be bound by any particular theory of invention, it is believed that this lack of any substantial difference in drug release in the 10% and 25% drug load implants may be due to the fact that the entire release lasted only 12 days, which may be too rapid for any significant or meaningful differentiation to take place. Furthermore, it is believed that the use of Resomer RG502H may have contributed to the apparent lack of differentiation. Drug load and polymer formulation, or class, are each believed to be significant parameters for controlling the duration of drug release as well as controlling the initial burst effect for the drug. In order to test this theory, a series of formulations were made using Resomer RG503, RG504, RG505, RG506, RG752, RG755, RG756, RG858, R203, R206, and R208 each with a 10% drug load to compare the various polymer matrices. The release profiles are shown in FIGS. 5A, 5B, and 5C, based on the different classes of polymers.

As shown in Tables 5A, 5B and 5C, 50:50 poly (D,L-lactide-co-glycolide) polymers, in general, have approximately one-month release, 75:25 poly (D,L-lactide-co-glycolide) and 85:15 poly (D,L-lactide-co-glycolide) have approximately two-months release and the poly (D,L-lactides) have about three-month release or longer.

During this release study, it was noticed that certain formulations appeared to have drug releases higher than 100% of theory at the end of the study. It is not unusual in these studies to sometimes obtain an apparent total percent release greater than 100%. This may be explained as follows. Timolol maleate is a salt, and the actual timolol content by weight is 73.16% of the weight of salt. The HPLC standards can be prepared based on weight of timolol maleate salt (Mw 432), or based on the weight of timolol freebase (Mw 316) and then the weight of timolol maleate can be accordingly recalculated. Thus, to prepare a 1 µg/mL solution of timolol maleate, one weighs out 5 mg of timolol maleate which is then dissolved in 5 liters of medium. However, this 1 µg/mL solution timolol maleate actually contains only 0.73 µg/mL of timolol freebase. On the other hand, to prepare a 1 µg/mL solution of timolol freebase, one would have to weigh out 6.835 mg of timolol maleate salt, instead of 5 mg, which is then dissolved in 5 liter of medium.

Figure 6:
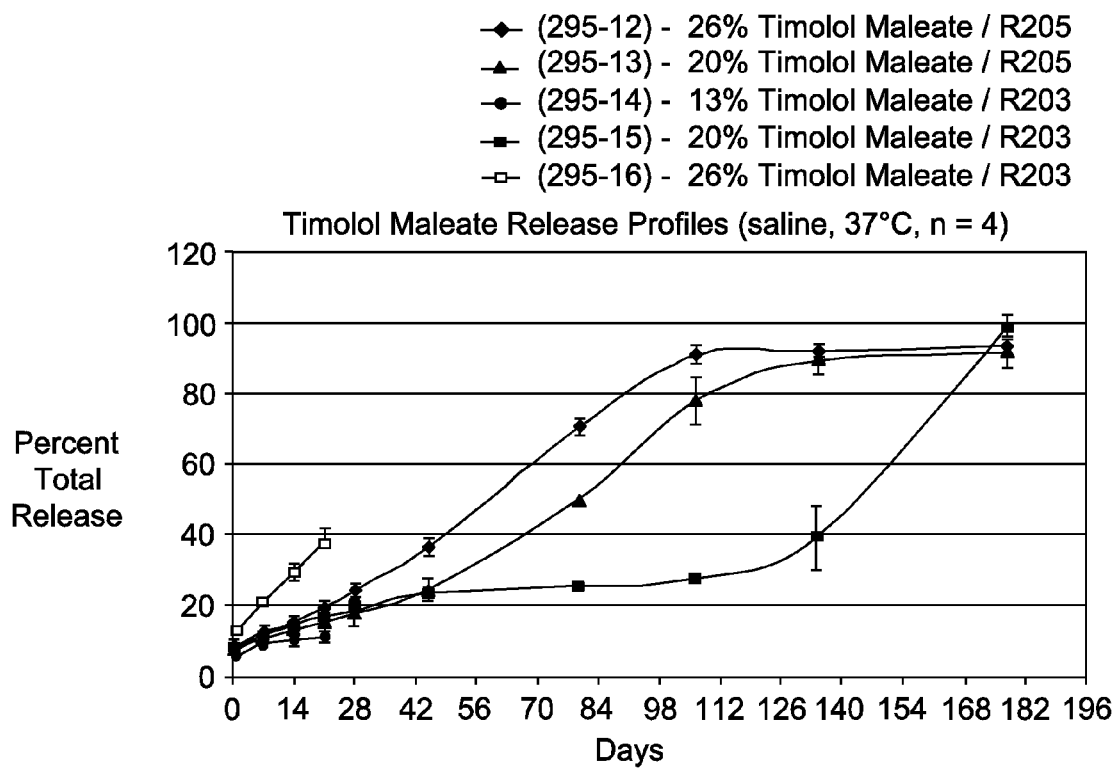
FIG. 6 is a graph of timolol maleate release profiles of drug delivery systems in accordance with the invention, comprising timolol maleate and a polymer, in which formulations were prepared with drug content based on the weight of timolol, rather than on the weight of timolol maleate.

Additional release profiles are shown in FIG. 6.

As shown, timolol maleate formulated with 20% drug load in R206 (lot 295-13) showed a steady release to 78% on day 106, then a slightly slower release reaching 89% on day 134, and finally leveling off gradually to 92% on day 177. Timolol maleate formulated with 26% drug load in R206 (lot 295-12) showed a steady release to 91% on day 106, faster than lot 295-13, then a slightly slower release reaching 92% on day 134, and remained essentially unchanged to 93% on day 177. In contrast, timolol maleate formulated with 20% drug load in R203 (lot 295-15) showed a slow release achieving only 28% on day 106, and reaching 39% by day 134, but then accelerated to 99% of total release on day 177.

Because the type of polymer will have an effect on the release rate of the active agent in the implants in accordance with the invention, it is contemplated that drug delivery system implants can be formulated to have a desired release rate by combining two or more polymers as a matrix material, with the active agent. The polymers are preferably selected to achieve a desired release rate of the active component from the implant.

For example, complimentary release characteristics can be utilized by combining two different polymers, for example wherein one polymer has a high release profile representing an upper limit on a desired release, and another polymer has a low release profile representing a lower limit on a desired release. For example, both polymer R203 and R206 with timolol maleate can be used to achieve a release rate that is more desirable with R203 or R206 alone. In other words, it can be appreciated that if 20% timolol maleate in R206 (295-13) is considered the upper limit of what we would like to achieve, while 20% timolol maleate in R203 is considered the lower limit, then a more desirable release profile somewhere between the two can be achieved when combining both polymers together in various proportions.

EXAMPLE 2

In Vivo Testing of Intraocular Implants Containing Timolol and a Biodegradable Polymer Matrix The first in-vivo study conducted on timolol formulation tested two different types of implants, both having a 10% drug load and a polymer of R206. The implants were the same implant formulations having the release profiles shown in FIG. 3. Both types were formulated with 10% timolol maleate in R206 polymer. A first type of the implant was in the form or a pellet, or rod, and the second type was in the form of a wafer.

The initial study was conducted on two animals. The rods from lot 241-179 were surgically implanted into the anterior chamber of the right eye and under conjuntiva of the left eye of the first animal. The wafers from lot 241-192 were surgically implanted into the anterior chamber ("AC") of the right eye and under conjuntiva of the left eye of the second animal. The anterior chamber sampling days were days 1, 4, 7, 12, 28, and every other week there after. No detectable levels of timolol were found for both lots up to day 47. On day 47, the two rods and two wafers were extracted from the animals and total content analysis performed. The results are summarized in Table 2.

TABLE 2

Timolol Maleate Total Content Determination (lot 241-179 & lot 241-192)

| Rabbit | Lot # | Sample Wt. µg | Theor. Tim. amount, µg | Tim conc. µg/mL | Timolol (µg) Recovered | Percent Recovery |
|---|---|---|---|---|---|---|
| 7473-OD | 241-179 | 1314 | 96.05 | 4.25 | 106.25 | 110.62 |
| 7473-OS | 241-179 | 1324 | 96.78 | 1.87 | 93.50 | 96.61 |
| 7474-OD | 241-192 | 1312 | 95.91 | 1.65 | 82.50 | 86.02 |
| 7474-OS | 241-192 | 1230 | 89.91 | 1.64 | 82.00 | 91.20 |

The implants were extracted from both animals and total content analysis of the remnants showed most of timolol maleate was still in the implants, which meant that only minute quantity of timolol maleate was released from the implants. This was a stark contrast to the in-vitro data, which, as described hereinabove with reference to FIG. 3, showed a release of 20.2% after 35 days for lot 241-179, and 15.8% after 35 days for lot 24-192. A possible explanation for the observed no release for these two lots was that perhaps the rods or wafers were too large in size, especially when implanted into the anterior chamber, which contains approximately 200-300 µL of aqueous humor, or subconjuntiva. Thus, relatively smaller implants with relatively higher drug load were used for the subsequent in-vivo study.

The second timolol in-vivo study conducted was on lot 241-173 with 25% timolol maleate (w/w) in R206. The study was conducted on one animal, both eyes were surgically implanted with implants (240 µg) in the anterior chamber and AC sampling was scheduled to be done after 1 hr, 6 hr, 48 hr, 7 days, 71 days and 75 days. The in-vivo data is shown in Table 3.

TABLE 3

Timolol Maleate Levels (µg/mL) in Rabbit (lot # 241-173)

| Rabbit | 1 hr | 6 hr | 24 hr | 48 hr | 7 day |
|---|---|---|---|---|---|
| 7477-D | 1.1 | 0.2 | 0.19 | 0.07 | 0.00 |
| 7477-S | 4.19 | 0.37 | 0.11 | 0.06 | 0.00 |
| Average | 2.65 | 0.29 | 0.15 | 0.07 | 0.00 |
| SD | 2.18 | 0.12 | 0.06 | 0.01 | 0.00 |

The levels were high initially, at about 2.65 µg/mL, probably due to the burst effect of the implant formulation, then the levels steadily dropped off to about 0.29 µg/mL, about 0.15 µg/mL, about 0.07 µg/mL, and about 0.00 µg/mL for 6 hr, 24 hr, 48 hr, and 7 day, respectively. It was not clear if the implants simply stopped releasing drug on day 7, since the in-vitro data (FIG. 2.) showed timolol release about 30% by day 7, or approximately 18 µg. One possible explanation was the rapid clearance rate of timolol maleate in rabbit eyes.

Hypothetically, if timolol maleate clearance rate in the eye equals the timolol maleate release rate from the polymer matrix, then the aqueous humor could yield no level when analyzed. The two implants were extracted from the animal after 75 days and their total content was determined. The results are summarized in Table 4. The total content showed about 89% of timolol maleate was released from the implant in the right eye and about 88% was released from the implant in the left eye after 75 days.

TABLE 4

Timolol Maleate Total Content Determination (lot 241-173)

| Rabbit | Lot # | Sample Wt. µg | Theor. Tim. amount, µg | Tim conc. µg/mL | Timolol (µg) Recovered | Percent Released |
|---|---|---|---|---|---|---|
| 7477-OD | 241-173 | 240 | 45.6 | 0.20 | 5.00 | 89.00 |
| 7477-OS | 241-173 | 240 | 45.6 | 0.22 | 5.50 | 87.90 |

In order to determine whether clearance rate was a possible explanation, a known quantity of a bolus injection of timolol maleate solution (1.5 mg in 25 µL) was injected into the eyes of 10 rabbits, five in the anterior chamber and the remaining five in the posterior segment. Sampling was done from the anterior chamber for the first five animals after 1 hr, 3 hr, 6 hr, 12 hr, and 24 hr, and from both the anterior chamber and posterior segment of the remaining five animals after 1 hr, 3 hr, 6 hr, 24 hr, and 48 hr. One animal was used for each time point. The data for the first five animals are shown in Table 5A, and the remaining five animals in Tables 5B and 5C.

TABLE 5A

Timolol Maleate Injection into Anterior Chamber (Levels in AC, µg/mL)

| Rabbit | 0 hr | 1 hr | 3 hr | 6 hr | 12 hr | 24 hr |
|---|---|---|---|---|---|---|
| 642-D | 1500 | 1191.7 | | | | |
| 642-S | 1500 | 485.16 | | | | |
| 628-D | 1500 | | 42.82 | | | |
| 628-S | 1500 | | 56.52 | | | |
| 623-D | 1500 | | | 0.82 | | |
| 623-S | 1500 | | | 1.49 | | |
| 636-D | 1500 | | | | 0.08 | |
| 636-S | 1500 | | | | 0.05 | |
| 643-D | 1500 | | | | | 0.02 |
| 643-S | 1500 | | | | | 0.04 |
| Average | 1500 | 838.43 | 49.67 | 1.16 | 0.07 | 0.03 |
| SD | | 499.60 | 9.69 | 0.47 | 0.02 | 0.01 |

TABLE 5B

Timolol Maleate Injection into Posterior Segment (Levels in PS, µg/mL)

| Rabbit | 0 hr | 1 hr | 3 hr | 6 hr | 24 hr | 48 hr |
|---|---|---|---|---|---|---|
| 635-D | 1500 | 744.31 | | | | |
| 635-S | 1500 | 706.34 | | | | |
| 641-D | 1500 | | 395.57 | | | |
| 641-S | 1500 | | 198.57 | | | |
| 640-D | 1500 | | | 125.69 | | |
| 640-S | 1500 | | | 104.68 | | |
| 637-D | 1500 | | | | 1.66 | |
| 637-S | 1500 | | | | 1.4 | |
| 639-D | 1500 | | | | | 0.69 |
| 639-S | 1500 | | | | | 0.15 |
| Average | 1500 | 725.33 | 297.07 | 115.19 | 1.53 | 0.42 |
| SD | | 26.85 | 139.30 | 14.86 | 0.18 | 0.38 |

TABLE 5C

Timolol Maleate Injection into Posterior Segment (Levels in AC, µg/mL)

| Rabbit | 0 hr | 1 hr | 3 hr | 6 hr | 24 hr | 48 hr |
|---|---|---|---|---|---|---|
| 635-D | | 0.75 | | | | |
| 635-S | | 0.16 | | | | |
| 641-D | | | 2.13 | | | |
| 641-S | | | 1.6 | | | |
| 640-D | | | | 0.78 | | |
| 640-S | | | | 0.53 | | |
| 637-D | | | | | 0.39 | |
| 637-S | | | | | 0.46 | |
| 639-D | | | | | | 0.43 |
| 639-S | | | | | | 0.16 |
| Average | | 0.46 | 1.87 | 0.66 | 0.43 | 0.30 |
| SD | | 0.42 | 0.37 | 0.18 | 0.05 | 0.19 |

The levels were high initially after the first hour at about 838 µg/mL. However, they dropped off dramatically after 3 hours, 6 hours, 12 hour and 24 hour to about 49.67 µg/mL, about 1.16 µg/mL, about 0.07 µg/mL, and about 0.03 µg/mL, respectively. The level at the 6 hour time point was only about 0.13% of that at one hour time point. Comparing this result to the levels at the same two time points for the timolol implant (295-173, Table 2), it was concluded that the clearance rate of timolol maleate in the anterior chamber may be a significant factor in measuring the levels. From this in-vivo study, the clearance rate of timolol maleate was calculated by taking the difference in levels between any two time points and divided it by the difference in time. i.e. between zero hour to the first hour, the clearance rate was calculated to be about 661 µg/hr, and between first hour to the third hour, the clearance rate was calculated to be about 394 µg/hr, and etc. From these, the half-life in rabbit anterior chamber was calculated to be about 1.43 hour.

The levels in the posterior segment after same bolus injection showed relatively slower clearance rate at the 1 hour time point and even much slower at subsequent time points, as presented in Table 5B. Detectable levels of timolol maleate were found in the anterior chamber from the posterior segment bolus injection, as shown in Table 5C, although the levels were small and considered insignificant.

Since it was difficult to determine the levels of timolol in the rabbit eyes even with bolus injection, we focused our attention on measuring intra-ocular pressure (IOP) to probe the efficacy of the implant.

This led to the fourth in-vivo study, which was designed for 9 animals. They were divided into three groups of three animals each. The timolol implants were placed into three different areas in the eyes, anterior chamber, posterior segment, and conjuntiva. Only the right eye of each animal received an implant, while the left eye was left alone as control. Intraocular pressure of both eyes of each rabbit was measured one week prior to the surgery as background, and days 1, 2, 3, 4, 7, and once a week up to six months post surgery. The formulation chosen was lot 295-16 (see FIG. 6), which was 26% timolol maleate in R203. This formulation was chosen for its seemingly zero order release profile up to 21 day of release. Prior to the surgery, the IOP of all nine animals were measured to obtain a baseline. The baseline IOP data for the animals is shown in Table 6.

TABLE 6

Baseline Intra-Ocular Pressure - Pre-surgery (mmHg)

| Rabbit | Day 1 | 2 | 3 | 4 | 5 | 8 | Average | SD |
|---|---|---|---|---|---|---|---|---|
| Anterior Chamber | | | | | | | | |
| 1682-OD | 23.5 | 18.5 | 19.0 | 18.0 | 18.5 | 19.5 | 19.5 | 2.0 |
| 1682-OS | 23.0 | 18.0 | 21.0 | 21.0 | 20.5 | 17.5 | 20.2 | 2.1 |
| 1697-OD | 19.0 | 19.0 | 18.0 | 17.5 | 18.5 | 15.0 | 17.8 | 1.5 |
| 1697-OS | 16.5 | 18.0 | 17.0 | 18.5 | 17.5 | 16.5 | 17.3 | 0.8 |
| 1689-OD | 16.0 | 18.0 | 20.0 | 19.0 | 19.0 | 18.5 | 18.4 | 1.4 |
| 1689-OS | 16.5 | 19.0 | 17.0 | 16.5 | 17.0 | 17.5 | 17.3 | 0.9 |
| Posterior Segment | | | | | | | | |
| 1696-OD | 15.0 | 19.5 | 15.0 | 16.5 | 15.0 | 16.0 | 16.2 | 1.8 |
| 1696-OS | 18.0 | 15.5 | 17.0 | 15.0 | 16.0 | 15.5 | 16.2 | 1.1 |
| 1698-OD | 19.5 | 18.5 | 19.5 | 20.0 | 19.5 | 19.5 | 19.4 | 0.5 |
| 1698-OS | 19.5 | 17.5 | 16.0 | 16.0 | 17.0 | 16.5 | 17.1 | 1.3 |
| 1683-OD | 20.5 | 21.0 | 20.0 | 20.5 | 19.0 | 20.0 | 20.2 | 0.7 |
| 1683-OS | 16.5 | 16.0 | 16.0 | 17.0 | 16.5 | 17.5 | 16.6 | 0.6 |
| Conjuntiva | | | | | | | | |
| 1694-OD | 22.5 | 21.5 | 21.0 | 18.5 | 18.5 | 17.0 | 19.8 | 2.1 |
| 1694-OS | 16.5 | 19.0 | 18.0 | 19.0 | 18.0 | 16.5 | 17.8 | 1.1 |
| 1693-OD | 15.5 | 15.0 | 15.0 | 14.5 | 15.0 | 15.0 | 15.0 | 0.3 |
| 1693-OS | 16.0 | 19.5 | 16.5 | 16.5 | 16.0 | 17.5 | 17.0 | 1.3 |
| 1685-OD | 18.0 | 14.5 | 16.0 | 18.5 | 18.0 | 14.5 | 16.6 | 1.8 |
| 1685-OS | 16.0 | 16.0 | 14.5 | 16.5 | 16.5 | 14.5 | 15.7 | 0.9 |

Figure 7:
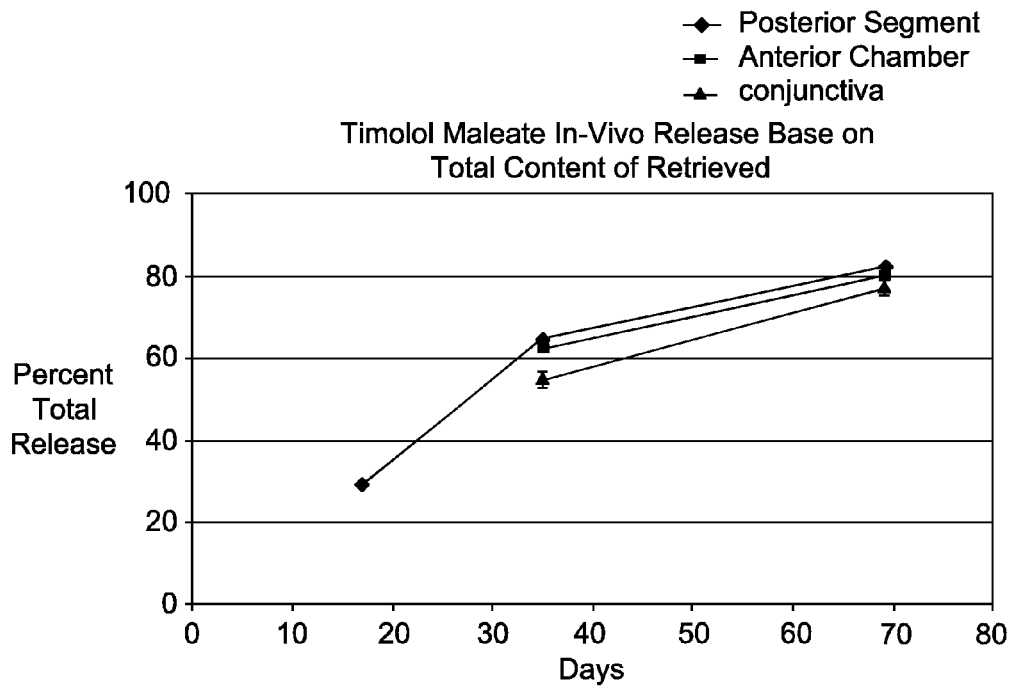
FIG. 7 is a graph showing timolol maleate in-vivo release based on total content of drug in drug delivery system retrieved after implantation.

As expected, the IOP of each animal fluctuated from day to day but over a period of 8 days it tend to equilibrated around in the high teens with standard deviation ranging from low of 0.3 to the high of 2.1. On day 15, one was found to be ill and thus, was sacrificed on day 17 and the remnant retrieved for total content analysis. On day 35 animal # 1693 (conjuntiva), animal # 1697 (anterior chamber) and animal # 1698 (posterior segment) were sacrificed, and on day 69, the remaining five animals were sacrificed and remnants removed for total content analysis. The results are presented in Table 7 and the release profiles based on recovered remnants at each time point is shown in FIG. 7.

TABLE 7

Timolol Maleate IN-Vivo Total Content

| Animal # | Wt. of DDS | Theor. timolol amount, (µg) | Day Sacrificed | Timolol (µg) Recovered | Timolol % Recovery | Timolol % Released |
|---|---|---|---|---|---|---|
| 1696 (PS) | 809 | 150.47 | 17 | 105.50 | 70.11 | 28.89 |
| 1693 (Conj) | 791 | 147.92 | 35 | 67.75 | 45.80 | 54.20 |
| 1697 (AC) | 769 | 143.80 | 35 | 55.00 | 38.25 | 61.75 |
| 1698 (PS) | 781 | 146.05 | 35 | 52.50 | 39.95 | 64.05 |
| 1694 (Conj) | 770 | 143.22 | 69 | 36.00 | 25.14 | 74.86 |
| 1689 (AC) | 763 | 141.92 | 69 | 29.00 | 20.43 | 79.57 |
| 1685 (Conj) | 807 | 150.10 | 69 | 33.50 | 22.32 | 77.68 |
| 1683 (PS) | 829 | 154.19 | 69 | 29.25 | 18.97 | 81.03 |
| 1682 (AC) | 765 | 142.29 | 69 | 30.25 | 21.26 | 78.74 |

As shown in FIG. 7, the data showed similar release profiles for all three locations, anterior chamber, posterior segment, and conjunctiva.

Figure 8:
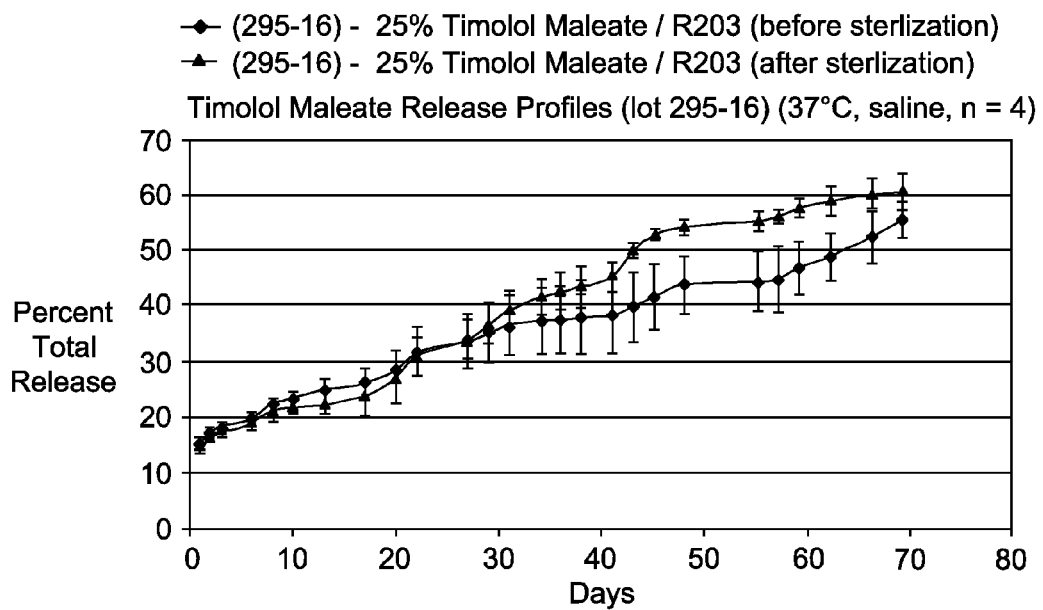
FIG. 8 is a graph showing timolol maleate release profiles of drug delivery systems in accordance with the invention, comprising timolol maleate and a polymer, the systems each having 26% drug load.

Comparison of the in-vivo profile with the in-vitro profile, shown in FIG. 8, a good correlation between the release profiles can be recognized.

The intra-ocular pressure of both the right and left eyes of the nine animals was measured on indicated days, as shown in Table 8.

TABLE 8

Timolol Maleate IOP Schedule

| Animal # | Day |
|---|---|
| 1696 | 1, 2, 3, 6, 7, 8, 9, 13, 15 |
| 1693, 1697, 1698 | 1, 2, 3, 6, 7, 8, 9, 13, 15, 17, 20, 22, 24, 27, 29, 31, 34 |
| 1682, 1683, 1685, 1689, 1695 | 1, 2, 3, 6, 7, 8, 9, 13, 15, 17, 20, 22, 24, 27, 29, 31, 34, 38, 42, 45, 48, 52, 56, 60, 64 |

Figure 9A:
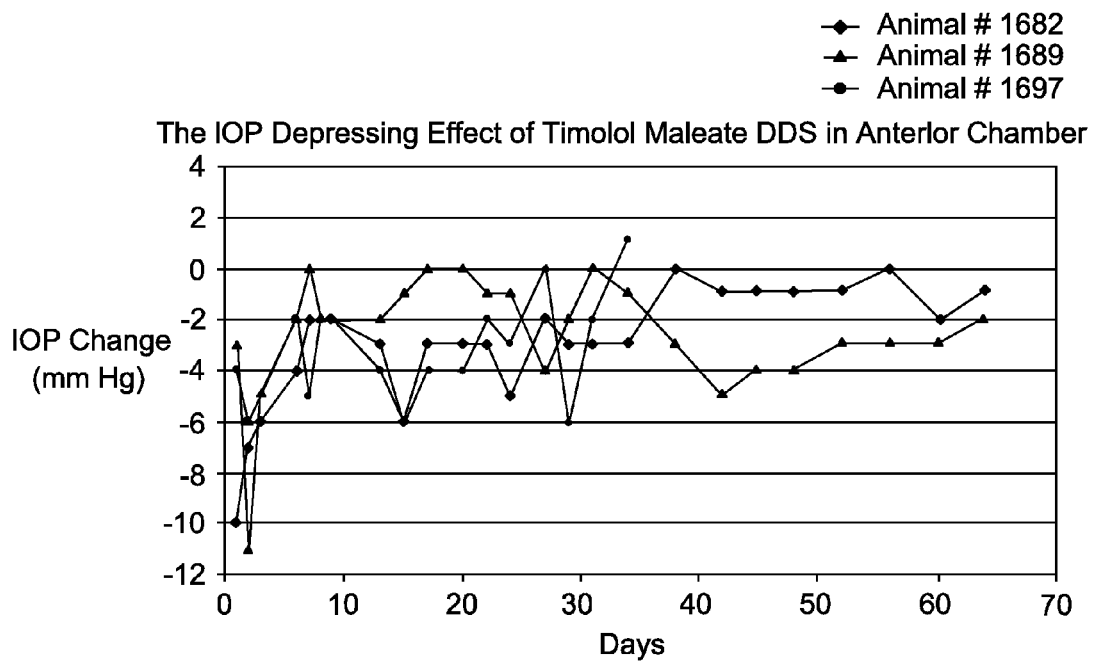
FIG. 9A is a graph showing intraocular pressure (IOP) depressing effect of timolol maleate drug delivery systems, in accordance with the present invention, placed in the anterior chamber of an eye.
Figure 9B:
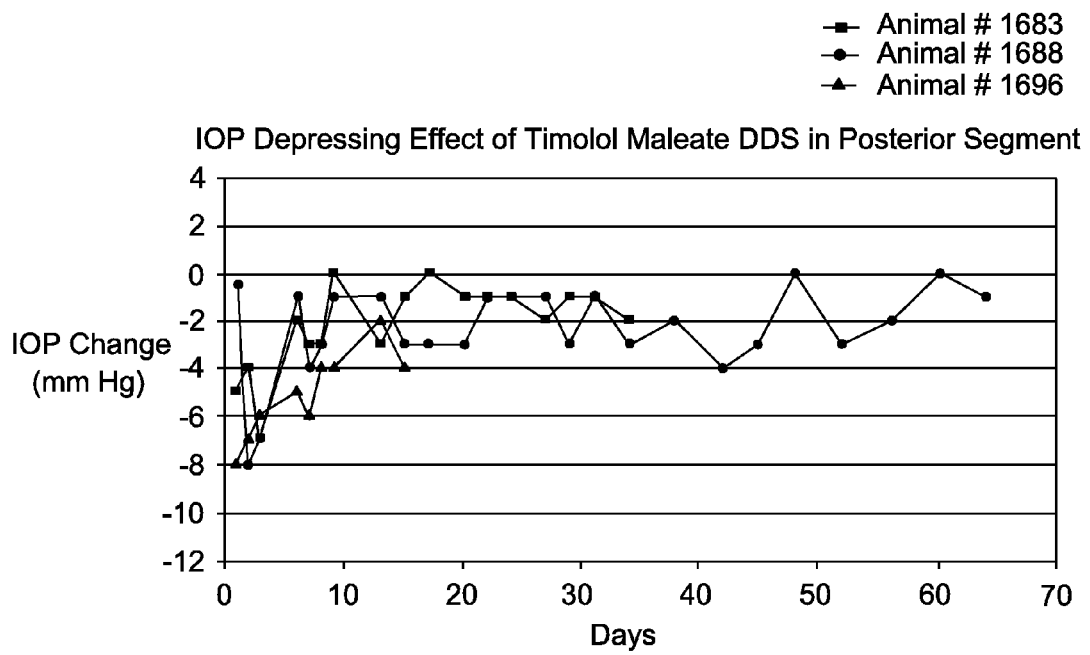
FIG. 9B is a graph showing IOP depressing effect of timolol maleate drug delivery systems, in accordance with the present invention, placed in the posterior segment of an eye.
Figure 9C:
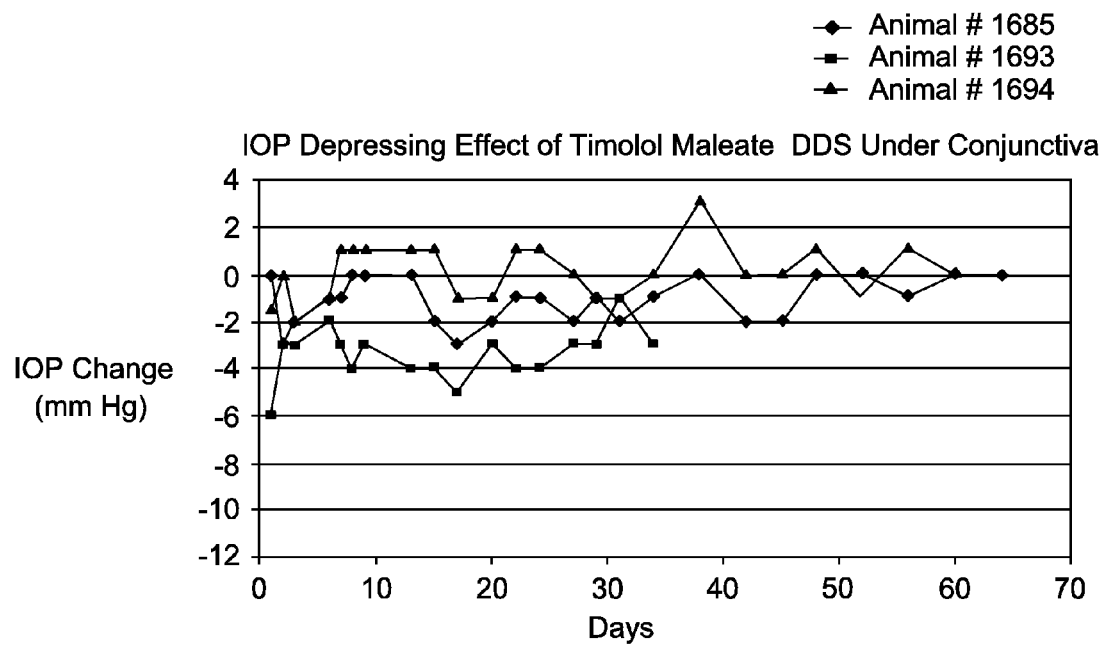
FIG. 9C is a graph showing IOP depressing effect of timolol maleate drug delivery systems, in accordance with the present invention, placed under the conjunctiva of an eye.

The data was collected in order to compensate for the IOP variations from eye to eye of each animal, both presurgery and post surgery, the IOP changes were calculated as follows:

$$\Delta\Delta IOP = \Delta IOP - \Delta IOP_{baseline} \quad (1)$$

$$\Delta IOP = \Delta IOP_{treated} - \Delta IOP_{controlled} \quad (2)$$

where $\Delta IOP_{treated}$ and $\Delta IOP_{controlled}$ controlled represent the IOP of treated (right) and controlled (left) eye, respectively. $\Delta IOP_{baseline}$ is the difference of IOP of both eyes at time 0. The IOP depressing effect of timolol maleate in anterior chamber, posterior segment, and conjunctiva are presented in FIGS. 9A, 9B, and 9C. As a guideline, it is noted that a relatively more negative value of the IOP change translates to better therapeutic effect and a value of zero translates to no measurable therapeutic effect.

Figure 10:
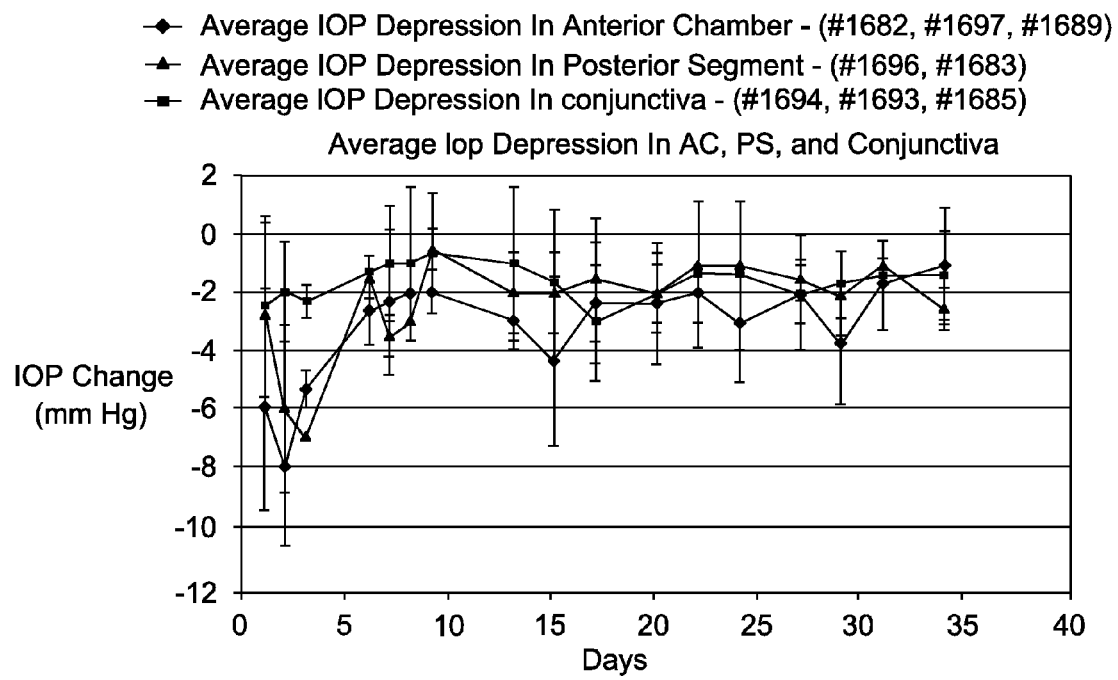
FIG. 10 is a graph showing average IOP depressing effect of timolol maleate drug delivery systems, in accordance with the present invention, placed in the posterior segment, in the anterior chamber, and under the conjunctiva of an eye.

The data showed that when timolol maleate implants, in accordance with the present invention, were surgically implanted into the anterior chamber of the eye, the resulting IOP depressing effect was most pronounced in each of the three locations in the eye. Additionally, it was concluded that implantation into the posterior segment seemed to be the second most effective in reducing IOP, and implantation into the conjunctiva appeared to be the least effective of the three locations in terms of effectiveness in depressing IOP. The average IOP depression in the anterior chamber, posterior segment and conjunctiva was calculated. This calculation is presented in FIG. 10.

This study seems to indicate that the most effective location for the implantation of timolol drug delivery systems or implants in accordance with the present invention is in the anterior chamber.

In order to determine what the average IOP depression would be for an eye that had the therapeutic levels of timolol, we used commercially available timolol eye drops and follow the recommended regiments as described below.

Figure 11:
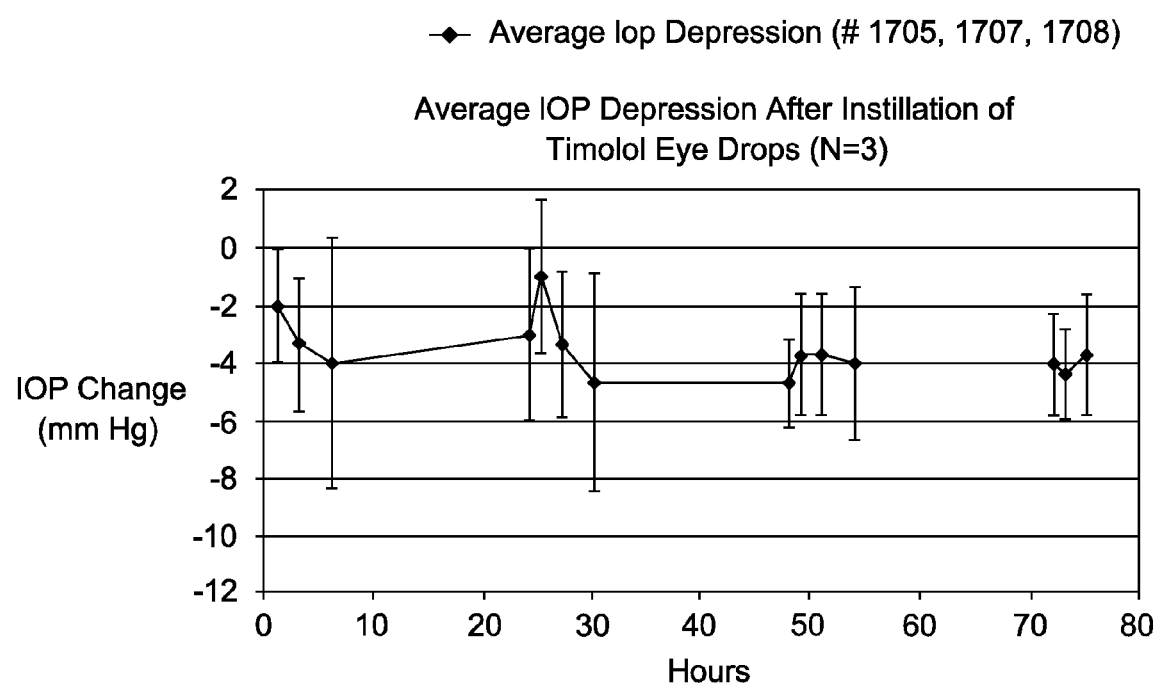
FIG. 11 is a graph showing average Iop depression after instillation of timolol eye drops (N=3)

In the fifth and final in-vivo study, three animals were used. Each animal's right eye was instilled with two drops of 0.5% Timolol eye drops in the morning and left eye as control, and IOP of both eyes were measured at 1 h, 3 h, and 6 h. This was repeated for two days. Using the same equations (1) and (2) to calculate the $\Delta IOP$ and $\Delta\Delta IOP$. The average IOP depression of the three animals is shown in FIG. 11.

As shown in a marked IOP depression was observed at about 6 hour after instillation on the first day, but such a depression was not observed on the second day. It seemed the average IOP depression was localized around −2 mm Hg range, which was similar to what was observed with the implant formulations of the present invention which comprised about 26% timolol maleate in R203 polymer (lot 295-16).

Conclusions

Timolol maleate implants in accordance with the present invention which were formulated with poly (D,L-lactide) Resomer R206 and/or Resomer R203 (lot 295-15), have provided a in vitro release profile of about six months. Due to its high water solubility, timolol maleate exhibits very quick release profiles using poly (lactide-co-glycolide) of various viscosities. It was found that drug load was a major contributing factor that facilitated the rapid release of timolol maleate in aqueous medium. If the drug load was reduced from 50% down to 10-20% range, effective sustained release from 3-6 months could be achieved.

The first timolol formulation selected for the animal study was 10% timolol maleate in R203 as rods (lot 241-179) and as wafers (lot 241-192). Unfortunately, timolol were detected and after total content determination was made, it was found that all timolol maleate were still in the drug delivery implants and no detectable levels were released. This was different from the in-vitro release profiles, which showed about 20.2% release for the rods and about 15.8% release for the wafers after about 35 days. It was reasoned that perhaps the size of the implants (1300 µg) was too large to be effective when implanted in the anterior chamber. Using smaller implants, the next in-vivo study utilized implants of about 26% timolol maleate in R203 (lot 295-16) and the implant size was reduced to about 240 μm.

Further in-vivo studies demonstrated that polymer/timolol implants in accordance with the invention that were implanted into the anterior chamber of the eye exhibited better therapeutic levels than identical implants implanted into either the posterior segment or the conjuntiva of the eye, as indicated by more negative IOP depression values. Further, these depression values were similar to that obtained with implants formulated with 26% timolol maleate in R203 (lot 295-16). From this, it was inferred that 26% timolol maleate in R203 (lot 295-16) probably provided therapeutic levels to effectively depress IOP.

EXAMPLE 3

A 72 year old woman is diagnosed with age related open angle glaucoma that is becoming progressively worse. Her intraocular pressure ranges between about 26 mm Hg and about 28 mm Hg. An implant containing 15% timolol maleate in a matrix comprising equal amounts (a 1:1 ratio) of biodegradable polymers (R203 and R206 is placed into the vitreous of both of the woman's eyes using a trocar. Over the next several days, the physician measures the intraocular pressure in the eyes and finds that the intraocular pressure appears to be decreasing and becomes steady at about 20 mm Hg. The woman also reports that she notices a decrease in discomfort in her eyes. The implants continue to provide a relatively consistent, effective dose of timolol to the eyes over the next 4 months. At about the fifth month, the physician measures the intraocular pressure and determines that the implants no longer seem to be maintaining the desired intraocular pressure in the woman's eyes. It is presumed that the implants have degraded completely. The physician repeats the procedure every 5 months for the remainder of the woman's life. The implants in accordance with the invention prevent any significant further loss of vision for the woman.

The implants disclosed herein may also be configured to release additional therapeutic agents, as described above, which may be effective in treating diseases or conditions, such as the following:

MACULOPATHIES/RETINAL DEGENERATION: Non-Exudative Age Related Macular Degeneration (ARMD), Exudative Age Related Macular Degeneration (ARMD), Choroidal Neovascularization, Diabetic Retinopathy, Acute Macular Neuroretinopathy, Central Serous Chorioretinopathy, Cystoid Macular Edema, Diabetic Macular Edema.

UVEITIS/RETINITIS/CHOROIDITIS: Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpignous Choroiditis, Subretinal Fibrosis and Uveitis Syndrome, Vogt-Koyanagi-Harada Syndrome.

VASCULAR DISEASES/EXUDATIVE DISEASES: Coat's Disease, Parafoveal Telangiectasis, Papillophlebitis, Frosted Branch Angitis, Sickle Cell Retinopathy and other Hemoglobinopathies, Angioid Streaks, Familial Exudative Vitreoretinopathy.

TRAUMATIC/SURGICAL: Sympathetic Ophthalmia, Uveitic Retinal Disease, Retinal Detachment, Trauma, Laser, PDT, Photocoagulation, Hyperfusion During Surgery, Radiation Retinopathy, Bone Marrow Transplant Retinopathy.

PROLIFERATIVE DISORDERS: Proliferative Vitreal Retinopathy and Epiretinal Membranes, Proliferative Diabetic Retinopathy.

INFECTIOUS DISORDERS: Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associated with HIV Infection, Uveitic Disease Associated with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis.

GENETIC DISORDERS: Retinitis Pigmentosa, Systemic Disorders with Accosiated Retinal Dystrophies, Congenital Stationary Night Blindness, Cone Dystrophies, Stargardt's Disease and Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum.

RETINAL TEARS/HOLES: Retinal Detachment, Macular Hole, Giant Retinal Tear.

TUMORS: Retinal Disease Associated with Tumors, Congenital Hypertrophy of the RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

MISCELLANEOUS: Punctate Inner Choroidopathy, Acute Posterior Multifocal Placoid Pigment Epitheliopathy, Myopic Retinal Degeneration, Acute Retinal Pigment Epithelitis and the like.

All references, articles, publications and patents and patent applications cited herein are incorporated by reference in their entireties.

While this invention has been described with respect to various specific examples and embodiments, it is to be understood that the invention is not limited thereto and that it can be variously practiced within the scope of the following claims.

We claim:

1. A method of reducing intraocular pressure in an eye of a patient, the method comprising the step of placing a biodegradable drug delivery implant in the anterior chamber of the eye of the patient, the implant consisting of 26% by weight timolol maleate in a poly(D,L-lactide) with an inherent viscosity of 0.3 dl/g, wherein said implant is an extruded filament and the total weight of said implant is about 250 μg, and wherein said implant provides a therapeutically effective amount of timolol maleate to the patient for at least about one week.

* * * * *

UNITED STATES PATENT AND TRADEMARK OFFICE
CERTIFICATE OF CORRECTION

PATENT NO. : 8,715,709 B2
APPLICATION NO. : 12/955630
DATED : May 6, 2014
INVENTOR(S) : Glenn T. Huang et al.

It is certified that error appears in the above-identified patent and that said Letters Patent is hereby corrected as shown below:

On the title page, item (56), under "Other Publications", in column 2, line 6, delete "Siration," and insert -- Stratton, --, therefor.

On the title page, item (56), under "Other Publications", in column 2, line 11, delete "Lotaprednoletabonate" and insert -- Loteprednoletabonate --, therefor.

On title page 2, item (56), under "Other Publications", in column 2, line 9, delete ""Lumiga®:" and insert -- "Lumigan®: --, therefor.

On title page 2, item (56), under "Other Publications", in column 2, line 22, delete "Subloveal" and insert -- Subfoveal --, therefor.

On title page 2, item (56), under "Other Publications", in column 2, line 29, delete "Claucoma"," and insert -- Glaucoma", --, therefor.

On title page 2, item (56), under "Other Publications", in column 2, line 34, delete "methoxycestradiol" and insert -- methoxyestradiol --, therefor.

On title page 3, item (56), under "Other Publications", in column 1, line 4, delete "Persepective"," and insert -- Perspective", --, therefor.

On title page 3, item (56), under "Other Publications", in column 1, line 14, delete ""Scieral" and insert -- "Scleral --, therefor.

On title page 3, item (56), under "Other Publications", in column 1, line 14, delete "Biodegadablepolymers" and insert -- Biodegradable Polymers --, therefor.

On title page 3, item (56), under "Other Publications", in column 1, line 21, delete "140." and insert -- 149. --, therefor.

On title page 3, item (56), under "Other Publications", in column 1, line 30, delete "Plymeric" and insert -- Polymeric --, therefor.

Signed and Sealed this
Seventh Day of October, 2014

Michelle K. Lee
*Deputy Director of the United States Patent and Trademark Office*

On title page 3, item (56), under "Other Publications", in column 1, line 41, delete "Tazarolene:" and insert -- Tazarotene: --, therefor.

On title page 3, item (56), under "Other Publications", in column 1, line 46, delete "(Polytactates" and insert -- (Polylactates: --, therefor.

On title page 3, item (56), under "Other Publications", in column 2, line 5, delete "apoptasis" and insert -- apoptosis --, therefor.

On title page 3, item (56), under "Other Publications", in column 2, line 8, delete "prsesure" and insert -- pressure --, therefor.

On title page 3, item (56), under "Other Publications", in column 2, line 20, delete "Lalanoprost" and insert -- Latanoprost --, therefor.

On title page 3, item (56), under "Other Publications", in column 2, line 35, delete "Bimatoprosl" and insert -- Bimatoprost --, therefor.

On title page 3, item (56), under "Other Publications", in column 2, line 46, delete "Disk,"" and insert -- Disks," --, therefor.

On title page 3, item (56), under "Other Publications", in column 2, line 49, delete "Fluorouacil"," and insert -- Fluorouracil", --, therefor.

On title page 3, item (56), under "Other Publications", in column 2, line 57, delete "Alphagano P," and insert -- Alphagan® P, --, therefor.

On title page 3, item (56), under "Other Publications", in column 2, line 70, delete "Ophthalmol" and insert -- Ophthalmic --, therefor.

In the Specification

In column 1, line 54, delete "regiment" and insert -- regimen --, therefor.

In column 1, line 56, delete "(Timoptic®" and insert -- (Timoptic XE® --, therefor.

In column 2, line 13, delete "adengergic" and insert -- adrenergic --, therefor.

In column 3, line 39, delete "they" and insert -- the --, therefor.

In column 4, line 40, delete "lop" and insert -- IOP --, therefor.

In column 4, line 41, delete "(N=3)" and insert -- (N=3). --, therefor.

In column 6, line 34, delete "opthalmia;" and insert -- ophthalmia; --, therefor.

In column 7, line 30, delete "metiprenolol," and insert -- metipranolol, --, therefor.

In column 12, line 14, delete "loradatine," and insert -- loratadine, --, therefor.

In column 12, lines 18-19, delete "trimprazine" and insert -- trimeprazine --, therefor.

In column 12, line 44, delete "hexacatonide," and insert -- hexacetonide, --, therefor.

In column 12, line 48, delete "duanorubicin," and insert -- daunorubicin, --, therefor.

In column 12, line 56, delete "immunosuppresive" and insert -- immunosuppressive --, therefor.

CERTIFICATE OF CORRECTION (continued)
U.S. Pat. No. 8,715,709 B2

In column 12, line 60, delete "valciclovir," and insert -- valacyclovir, --, therefor.

In column 12, line 60, delete "phooosphonoformic" and insert -- phosphonoformic --, therefor.

In column 12, line 65, delete "cryotpxanthin, astazanthin," and insert -- cryptoxanthin, astaxanthin, --, therefor.

In column 12, line 67, delete "quercitin," and insert -- quercetin, --, therefor.

In column 16, line 16, delete "lnertsil," and insert -- Inertsil, --, therefor.

In column 19, line 19, delete "conjuntiva" and insert -- conjunctiva --, therefor.

In column 19, line 22, delete "conjuntiva" and insert -- conjunctiva --, therefor.

In column 19, line 62, delete "subconjuntiva." and insert -- subconjunctiva. --, therefor.

In column 22, line 22, delete "conjuntiva." and insert -- conjunctiva. --, therefor.

In column 22, line 53, delete "Conjuntiva" and insert -- Conjunctiva --, therefor.

In column 22, line 65, delete "(conjuntiva)," and insert -- (conjunctiva), --, therefor.

In column 23, line 23, delete "conjuntiva." and insert -- conjunctiva. --, therefor.

In column 24, line 3, delete "conjuntiva" and insert -- conjunctiva --, therefor.

In column 25, line 9, delete "conjuntiva" and insert -- conjunctiva --, therefor.

In column 25, line 57, delete "Serpignous" and insert -- Serpiginous --, therefor.

In column 25, line 60, delete "Telangiectasis," and insert -- Telangiectasias, --, therefor.

In column 26, line 22, delete "Accosiated" and insert -- Associated --, therefor.